United States Patent
Rose et al.

(10) Patent No.: US 6,767,923 B2
(45) Date of Patent: Jul. 27, 2004

(54) BENZHYDRYL DERIVATIVES

(75) Inventors: Ingo Rose, Mannheim (DE); Jordi Tormo i Blasco, Limburgerhof (DE); Markus Gewehr, Kastellaun (DE); Wassilios Grammenos, Ludwigshafen (DE); Bernd Müller, Frankenthal (DE); Joachim Rheinheimer, Ludwigshafen (DE); Peter Schäfer, Ottersheim (DE); Frank Schieweck, Hessheim (DE); Thomas Grote, Wachenheim (DE); Andreas Gypser, Mannheim (DE); Eberhard Ammermann, Heppenheim (DE); Gisela Lorenz, Hambach (DE); Reinhard Stierl, Mutterstadt (DE); Siegfried Strathmann, Limburgerhof (DE); Paul Carter, Wolfsheim (DE); Jürgen Curtze, Geisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/282,023

(22) Filed: Oct. 29, 2002

(65) Prior Publication Data

US 2003/0207938 A1 Nov. 6, 2003

(30) Foreign Application Priority Data

Oct. 31, 2001 (DE) .................................... 101 53 300

(51) Int. Cl.⁷ .................... A61K 31/215; C07C 43/205; C07C 43/21; C07C 43/215
(52) U.S. Cl. ................ 514/529; 514/648; 514/706; 514/721; 568/645; 568/62; 568/640; 568/641; 564/327; 560/238; 560/250; 560/255; 560/252
(58) Field of Search ................ 568/645, 640, 568/641, 62; 564/327; 560/238, 250, 255, 252; 514/529, 648, 706, 721

(56) References Cited

U.S. PATENT DOCUMENTS

| 3,340,294 A | 9/1967 | Richter et al. ............ 260/482 |
| 3,510,517 A | * 5/1970 | Mayer et al. ............... 564/327 |

FOREIGN PATENT DOCUMENTS

| EP | 0 015 756 | 9/1980 | ......... C07D/249/08 |
| EP | 0 461 079 | 12/1991 | ......... C07D/405/04 |
| EP | 0 727 141 | 8/1996 | .......... A01N/35/04 |
| EP | 0 801 048 | 10/1997 | ........... C07C/29/40 |
| GB | 1 218 623 | 1/1971 | ........... C07D/51/36 |
| JP | 09-235255 | * 9/1997 | ......... C07C/215/68 |

* cited by examiner

Primary Examiner—Rosalynd Keys
(74) Attorney, Agent, or Firm—Keil & Weinkauf

(57) ABSTRACT

Benzhydryl derivatives of the formula I,

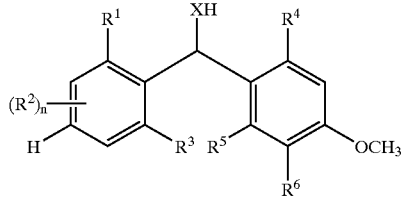

where the index and the variables are as defined below:

X is oxygen or sulfur;

$R^1$, $R^3$ are halogen, cyano, nitro, hydroxyl, mercapto, amino, alkyl, alkenyl, alkynyl, alkoxy, alkenyloxy, alkynyloxy, alkylcarbonyloxy, formyloxy, alkylthio, alkenylthio, alkynylthio, alkylamino, dialkylamino, alkylcarbonyl or formyl, where the carbon atoms in the radicals mentioned may be partially or fully halogenated;

$R^2$ is halogen, cyano, nitro, hydroxyl, mercapto, amino, alkyl, alkoxy, haloalkyl or haloalkoxy, where the groups $R^2$ may be different if n=2;

$R^4$ is alkyl, alkenyl or alkynyl, where the carbon atoms in these radicals may be unsubstituted or partially or fully halogenated;

$R^5$, $R^6$ are hydroxyl, alkyl, alkenyl, haloalkyl, haloalkenyl, alkoxy, alkenyloxy, haloalkoxy, haloalkenyloxy, cycloalkyl, cycloalkylalkyl, cycloalkoxy or cycloalkylalkoxy;

n is 0, 1 or 2;

processes for preparing the compounds I, compositions comprising them and their use for controlling phytopathogenic harmful fungi are described.

9 Claims, No Drawings

BENZHYDRYL DERIVATIVES

DESCRIPTION

The invention relates to benzhydryl derivatives of the formula I,

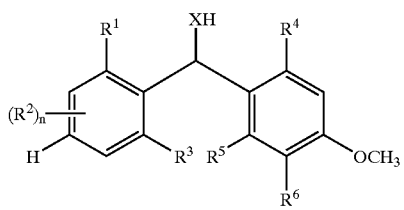

where the index and the variables are as defined below:
X is oxygen or sulfur;
$R^1$, $R^3$ are halogen, cyano, nitro, hydroxyl, mercapto, amino,
$C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkylcarbonyloxy, formyloxy, $C_1$–$C_6$-alkylthio, $C_2$–$C_6$-alkenylthio, $C_2$–$C_6$-alkynylthio, $C_1$–$C_6$-alkylamino, di-$C_1$–$C_6$-alkylamino, $C_1$–$C_6$-alkylcarbonyl or formyl, where the carbon atoms in the radicals mentioned may be partially or fully halogenated;
$R^2$ is halogen, cyano, nitro, hydroxyl, mercapto, amino, $C_1$–$C_6$-alkyl, $C_1$–$C_6$-alkoxy, $C_1$–$C_6$-haloalkyl or $C_1$–$C_6$-haloalkoxy, where the groups $R^2$ may be different if n=2;
$R^4$ is $C_1$–$C_6$-alkyl, $C_2$–$C_6$-alkenyl or $C_2$–$C_6$-alkynyl, where the carbon atoms in these radicals may be unsubstituted or partially or fully halogenated;
$R^5$, $R^6$ are hydroxyl, $C_1$–$C_6$-alkyl, $C_2$–$C_6$-alkenyl, $C_1$–$C_6$-haloalkyl, $C_2$–$C_6$-haloalkenyl, $C_1$–$C_6$-alkoxy, $C_2$–$C_6$-alkenyloxy, $C_1$–$C_6$-haloalkoxy, $C_2$–$C_6$-haloalkenyloxy, $C_3$–$C_8$-cycloalkyl, $C_3$–$C_8$-cycloalkyl-$C_1$–$C_3$-alkyl, $C_3$–$C_8$-cycloalkoxy or $C_3$–$C_8$-cycloalkyl-$C_1$–$C_3$-alkoxy;
n is 0, 1 or 2.

Additionally, the invention relates to processes for preparing the compounds I, to compositions comprising them and to the use of the compounds I for controlling phytopathogenic fungi.

In JP 08225474 various benzhydryl alcohols have been described as starting materials for pharmaceutics.

EP-A 461 079 discloses various benzhydryl alcohols having herbicidal action.

Benzhydryl alcohols having fungicidal action are already known, for example
(RS)-2,4'-difluoro-alpha-(1H-1,2,4-triazol-1-ylmethyl) benzhydryl alcohol (flutriafol; EP-A 015 756) or
(R,S)-2,4'-dichloro-alpha-(pyrimidin-5-yl)benzhydryl alcohol (fenarimol; GB 1 218 623). However, their action is not entirely satisfactory.

Benzophenones having fungicidal action are known from EP-A 727 141.

It is an object of the present invention to provide benzhydryl derivatives having a higher efficacy in the control of harmful fungi.

We have found that this object is achieved by the benzhydryl derivatives of the formula I. Furthermore, we have found processes for preparing the compounds I and compositions comprising them for controlling harmful fungi.

The compounds of the formula I differ from the benzhydryl alcohols disclosed in JP 08225474 by the substitution pattern on the phenyl rings.

The compounds of the formula I differ from the herbicidally active benzhydryl alcohols disclosed in EP-A 461 079 by the substituents of the phenyl rings, which substituents are fixed in positions 2, 2, 2', 2', 3', 4 and 4'.

The compounds of the formula I are secondary alcohols or thiols, whereas the compounds disclosed in EP-A 015 756 and GB 1 218 623 are tertiary alcohols which furthermore differ from compounds of the formula I in the substitution pattern on the phenyl rings.

The compounds of the formula I differ from the fungicidally active benzophenones disclosed in EP-A 727 141 in that the keto group is replaced by an alcohol or thiol function, and by the substitution patterns on the phenyl rings.

In the definitions of the symbols given in the formulae above, collective terms were used which, in general, represent the following substituents:

Halogen: fluorine, chlorine, bromine or iodine, preferably chlorine or bromine;

Alkyl: saturated, straight-chain or branched hydrocarbon radicals having 1 to 4 or 1 to 6 carbon atoms, for example $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 6 carbon atoms (as mentioned above), it being possible for some or all of the hydrogen atoms in these groups to be replaced by halogen atoms as mentioned above, for example $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 6 carbon atoms (as mentioned above), which are attached to the phenyl ring via an oxygen atom (—O—);

Haloalkoxy: straight-chain or branched haloalkyl groups having 1 to 6 carbon atoms (as mentioned above) which are attached to the phenyl ring via an oxygen atom (—O—);

Alkylthio: straight-chain or branched alkyl groups having 1 to 6 or 1 to 4 carbon atoms (as mentioned above) which are attached to the phenyl ring via a sulfur atom (—S—);

Alkylamino: a straight-chain or branched alkyl group having 1 to 6 carbon atoms (as mentioned above) which is attached to the phenyl ring via an amino group (—NH—);

Dialkylamino: two independent straight-chain or branched alkyl groups having in each case 1 to 6 carbon atoms (as mentioned above) which are attached to the phenyl ring via a nitrogen atom;

Alkylcarbonyloxy: a straight-chain or branched alkyl group having 1 to 6 carbon atoms (as mentioned above) which is attached to the phenyl ring via a carbonyloxy group (—CO$_2$—);

Alkenyl: unsaturated, straight-chain or branched hydrocarbon radicals having 2 to 6 carbon atoms and a double bond in any position, for example $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 2 to 6 carbon atoms and a double bond in any position (as mentioned above), it being possible for some or all of the hydrogen atoms in these groups to be replaced by halogen atoms as mentioned above, in particular by fluorine, chlorine and bromine;

Alkenyloxy: unsaturated, straight-chain or branched hydrocarbon radicals having 2 to 6 carbon atoms and a double bond in any position which is not adjacent to the heteroatom (as mentioned above), which are attached to the phenyl ring via an oxygen atom (—O—);

Haloalkenyloxy: unsaturated, straight-chain or branched alkenyloxy groups having 3 to 6 carbon atoms (as mentioned above), it being possible for some or all of the hydrogen atoms in these groups to be replaced by halogen atoms as mentioned above, in particular by fluorine, chlorine and bromine;

Alkenylthio: unsaturated, straight-chain or branched hydrocarbon radicals having 2 to 6 carbon atoms and a double bond in any position which is not adjacent to the heteroatom (as mentioned above), which are attached to the phenyl ring via a sulfur atom (—S—);

Alkynyl: straight-chain or branched hydrocarbon groups having 2 to 6 carbon atoms and a triple bond in any position, for example $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Alkynyloxy: unsaturated, straight-chain or branched hydrocarbon radicals having 3 to 6 carbon atoms and a triple bond in any position which is not adjacent to the heteroatom (as mentioned above), which are attached to the skeleton via an oxygen atom (—O—);

Alkynylthio: unsaturated, straight-chain or branched hydrocarbon radicals having 3 to 6 carbon atoms and a triple bond in any position which is not adjacent to the heteroatom (as mentioned above), which are attached to the skeleton via a sulfur atom (—S—).

With respect to the intended use of the benzhydryl compounds of the formula I, the following meanings of the substituents are particularly preferred, in each case on their own or in combination:

Benzhydryl derivatives of the formula I as claimed in claim 1 where the variables are as defined below:

X is oxygen or sulfur;

$R^1$, $R^3$ independently of one another are halogen, hydroxyl, mercapto, amino, $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, $C_1$–$C_6$-alkoxy, $C_2$–$C_6$-alkenyloxy, $C_2$–$C_6$-alkynyloxy, $C_1$–$C_6$-haloalkoxy, $C_2$–$C_6$-haloalkenyloxy, $C_2$–$C_6$-haloalkynyloxy, $C_1$–$C_6$-alkylcarbonyloxy, $C_1$–$C_6$-haloalkylcarbonyloxy, formyloxy, $C_1$–$C_6$-alkylthio, $C_2$–$C_6$-alkenylthio, $C_2$–$C_6$-alkynylthio, $C_1$–$C_6$-haloalkylthio, $C_2$–$C_6$-haloalkenylthio, $C_2$–$C_6$-haloalkynylthio, $C_1$–$C_6$-alkylamino, di-$C_1$–$C_6$-alkylamino, $C_1$–$C_6$-haloalkylamino, di-$C_1$–$C_6$-haloalkylamino, $C_1$–$C_6$-alkylcarbonyl, $C_1$–$C_6$-haloalkylcarbonyl or formyl;

$R^2$ is halogen, hydroxyl, $C_1$–$C_6$-alkyl, $C_1$–$C_6$-alkoxy, $C_1$–$C_6$-haloalkyl or $C_1$–$C_6$-haloalkoxy, where the radicals $R^2$ may be different if n=2;

$R^4$ is $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl or $C_2$–$C_6$-haloalkynyl;

$R^5$, $R^6$ independently of one another are hydroxyl, $C_1$–$C_6$-alkoxy, $C_2$–$C_6$-alkenyloxy, $C_1$–$C_6$-haloalkoxy or $C_2$–$C_6$-haloalkenyloxy;

n is 0, 1 or 2.

Particular preference is given to compounds I in which X is oxygen or sulfur;

$R^1$ and $R^3$ independently of one another are halogen, hydroxyl, mercapto, amino, $C_1$–$C_6$-alkyl, $C_1$–$C_6$-haloalkyl, $C_1$–$C_6$-alkoxy, $C_1$–$C_6$-haloalkoxy or $C_1$–$C_6$-alkylcarbonyl;

$R^2$ is halogen, hydroxyl, $C_1$–$C_6$-alkyl, $C_1$–$C_6$-haloalkyl, $C_1$–$C_6$-alkoxy or $C_1$–$C_6$-haloalkoxy, where the radicals $R^2$ may be different if n=2;

$R^4$ is methyl;

$R^5$, $R^6$ independently of one another are hydroxyl, $C_1$–$C_6$-alkoxy, $C_2$–$C_6$-alkenyloxy, $C_1$–$C_6$-haloalkoxy or $C_2$–$C_6$-haloalkenyloxy and n is 0 or 1.

Especially preferred are compounds I in which X is oxygen.

Preference is furthermore given to compounds I in which $R^1$ and $R^3$ independently of one another are halogen, hydroxyl, amino, mercapto, nitro, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylcarbonyloxy, $C_1$–$C_6$-haloalkylcarbonyloxy, $C_1$–$C_6$-alkylthio, $C_1$–$C_6$-haloalkylthio, $C_1$–$C_6$-alkylcarbonyl or $C_1$–$C_6$-haloalkylcarbonyl. Here, particular mention may be made of: fluorine, chlorine, bromine or iodine, hydroxyl, mercapto, amino, methyl, ethyl, methoxy, ethoxy, methylcarbonyloxy, ethylcarbonyloxy, methylthio, ethylthio, trifluoromethyl, difluoromethoxy or chlorofluoromethoxy.

In addition, preference is given to compounds I in which $R^1$ and $R^3$ independently of one another are halogen, hydroxyl, mercapto, amino, $C_1$–$C_6$-alkyl, $C_1$–$C_6$-haloalkyl, $C_1$–$C_6$-alkoxy or $C_1$–$C_6$-haloalkoxy. Here, particular mention may be made of: fluorine, chlorine, bromine or iodine, hydroxyl, mercapto, amino, methyl, ethyl, methoxy, ethoxy, trifluoromethyl, difluoromethoxy or chlorofluoromethoxy.

Particular preference is furthermore given to compounds I in which $R^1$ and $R^3$ independently of one another are halogen, such as fluorine, chlorine, bromine or iodine, hydroxyl, $C_1$–$C_6$-alkyl, such as methyl or ethyl, $C_1$–$C_6$-alkoxy, such as methoxy or ethoxy, or $C_1$–$C_6$-alkylcarbonyloxy, such as methylcarbonyloxy or ethylcarbonyloxy.

In addition, particular preference is given to compounds I in which $R^1$ and $R^3$ independently of one another are halogen, such as fluorine, chlorine, bromine or iodine, hydroxyl, $C_1$–$C_6$-alkyl, such as methyl or ethyl, or $C_1$–$C_6$-alkoxy, such as methoxy or ethoxy.

Very particular preference is given to compounds I in which $R^1$ and $R^3$ independently of one another are halogen, such as chlorine or bromine, or $C_1$–$C_6$-alkyl, such as methyl or ethyl.

Likewise, very particular preference is given to compounds I in which $R^1$ and $R^3$ independently of one another are hydroxyl, $C_1$–$C_6$-alkoxy, such as methoxy or ethoxy, or $C_1$–$C_6$-alkylcarbonyloxy, such as methylcarbonyloxy or ethylcarbonyloxy.

In addition, very particular preference is given to compounds I in which $R^1$ and $R^3$ independently of one another are hydroxyl or $C_1$–$C_6$-alkoxy, such as methoxy or ethoxy.

Moreover, preference is also given to compounds I in which $R^2$ is halogen, hydroxyl, $C_1$–$C_6$-alkyl, $C_1$–$C_6$-haloalkyl, $C_1$–$C_6$-alkoxy or $C_1$–$C_6$-haloalkoxy, where the groups $R^2$ may be different if n=2. Here, particular mention may be made of: fluorine, chlorine, bromine, iodine, methyl, ethyl, trifluoromethyl, difluoromethoxy, chlorofluoromethoxy.

Especially preferred are also compounds I in which $R^2$ is halogen, hydroxyl or $C_1$–$C_6$-alkoxy, such as methoxy or ethoxy.

Very particular preference is given to compounds I in which $R^2$ is halogen, in particular bromine or chlorine.

Moreover, particular preference is given to compounds I in which $R^4$ is $C_1$–$C_6$-alkyl or $C_1$–$C_6$-haloalkyl. Here, particular mention may be made of: methyl, ethyl and trifluoromethyl.

Especially preferred are compounds I in which $R^4$ is methyl.

Moreover, particular preference is given to compounds I in which $R^5$ and $R^6$ independently of one another are hydroxyl, $C_1$–$C_6$-alkoxy, $C_2$–$C_6$-alkenyloxy, $C_1$–$C_6$-haloalkoxy or $C_2$–$C_6$-haloalkenyloxy. Here, particular mention may be made of: hydroxyl, methoxy, ethoxy, n-propoxy, isopropoxy, butoxy, pentoxy, hexoxy, propenyloxy, trifluoromethoxy, difluoromethoxy and chlorofluoromethoxy.

Particular preference is furthermore given to compounds I in which $R^5$ and $R^6$ independently of one another are hydroxyl or $C_1$–$C_6$-alkoxy, such as methoxy, ethoxy, propoxy, butoxy, pentoxy and hexoxy.

Very particular preference is given to compounds I in which $R^5$ and $R^6$ are methoxy.

In addition, particular preference is given to compounds I in which n is 0 or 1, very particularly preferably 1.

Very particular preference is given to compounds I in which $R^1$ and $R^3$ independently of one another are fluorine, chlorine, bromine, iodine, hydroxyl, mercapto, methylthio, amino, methyl, ethyl, trifluoromethyl, methoxy, difluoromethoxy, fluorochloromethoxy, trifluoromethoxy, methylcarbonyloxy or ethylcarbonyloxy, $R^2$ is fluorine, chlorine, bromine, iodine, hydroxyl, methyl, trifluoromethyl, methoxy, ethoxy, difluoromethoxy or chlorofluoromethoxy, $R^4$ is methyl, ethyl or trifluoromethyl, $R^5$ and $R^6$ independently of one another are hydroxyl, methoxy, ethoxy, n-propoxy, isopropoxy or n-butoxy and n is 0 or 1.

With respect to their use, particular preference is given to the compounds I-A compiled in the tables below. The groups mentioned in the tables for a substituent are furthermore in their own right, independently of the combination in which they are mentioned, a particularly preferred embodiment of the substituent in question.

Table 1

Compounds of formula I-A in which n is 0, $R^4$ is methyl and $R^6$ is methoxy and the combination of the radicals $R^1$, $R^3$ and $R^5$ for a compound corresponds in each case to one row of Table A Table 2

Compounds of the formula I-A in which n is 1, $R^2$ is 3-methyl, $R^4$ is methyl and $R^6$ is methoxy and the combination of the radicals $R^1$, $R^3$ and $R^5$ for a compound in each case corresponds to one row of Table A Table 3

Compounds of the formula I-A in which n is 1, $R^2$ is 5-methyl, $R^4$ is methyl and $R^6$ is methoxy and the combination of the radicals $R^1$, $R^3$ and $R^5$ for a compound in each case corresponds to one row of Table A, where $R^1$ is different from $R^3$ Table 4

Compounds of the formula I-A in which n is 1, $R^2$ is 3-trifluoromethyl, $R^4$ is methyl and $R^6$ is methoxy and the combination of the radicals $R^1$, $R^3$ and $R^5$ for a compound in each case corresponds to one row of Table A Table 5

Compounds of the formula I-A in which n is 1, $R^2$ is 5-trifluoromethyl, $R^4$ is methyl and $R^6$ is methoxy and the combination of the radicals $R^1$, $R^3$ and $R^5$ for a compound in each case corresponds to one row of Table A, where $R^1$ is different from $R^3$ Table 6

Compounds of the formula I-A in which n is 1, $R^2$ is 3-hydroxyl, $R^4$ is methyl and $R^6$ is methoxy and the combination of the radicals $R^1$, $R^3$ and $R^5$ for a compound in each case corresponds to one row of Table A Table 7

Compounds of the formula I-A in which n is 1, $R^2$ is 5-hydroxyl, $R^4$ is methyl and $R^6$ is methoxy and the combination of the radicals $R^1$, $R^3$ and $R^5$ for a compound in each case corresponds to one row of Table A, where $R^1$ is different from $R^3$ Table 8

Compounds of the formula I-A in which n is 1, $R^2$ is 3-methoxy, $R^4$ is methyl and $R^6$ is methoxy and the combination of the radicals $R^1$, $R^3$ and $R^5$ for a compound in each case corresponds to one row of Table A Table 9

Compounds of the formula I-A in which n is 1, $R^2$ is 5-methoxy, $R^4$ is methyl and $R^6$ is methoxy and the combination of the radicals $R^1$, $R^3$ and $R^5$ for a compound in each case corresponds to one row of Table A, where $R^1$ is different from $R^3$ Table 10

Compounds of the formula I-A in which n is 1, $R^2$ is 3-ethoxy, $R^4$ is methyl and $R^6$ is methoxy and the combination of the radicals $R^1$, $R^3$ and $R^5$ for a compound in each case corresponds to one row of Table A Table 11

Compounds of the formula I-A in which n is 1, $R^2$ is 5-ethoxy, $R^4$ is methyl and $R^6$ is methoxy and the combination of the radicals $R^1$, $R^3$ and $R^5$ for a compound in each case corresponds to one row of Table A, where $R^1$ is different from $R^3$ Table 12

Compounds of the formula I-A in which n is 1, $R^2$ is 3-difluoromethoxy, $R^4$ is methyl and $R^6$ is methoxy and the combination of the radicals $R^1$, $R^3$ and $R^5$ for a compound in each case corresponds to one row of Table A Table 13

Compounds of the formula I-A in which n is 1, $R^2$ is 5-difluoromethoxy, $R^4$ is methyl and $R^6$ is methoxy and the combination of the radicals $R^1$, $R^3$ and $R^5$ for a compound in each case corresponds to one row of Table A, where $R^1$ is different from $R^3$ Table 14

Compounds of the formula I-A in which n is 1, $R^2$ is 3-chlorofluoromethoxy, $R^4$ is methyl and $R^6$ is methoxy and the combination of the radicals $R^1$, $R^3$ and $R^5$ for a compound in each case corresponds to one row of Table A Table 15

Compounds of the formula I-A in which n is 1, $R^2$ is 5-chlorofluoromethoxy, $R^4$ is methyl and $R^6$ is methoxy and the combination of the radicals $R^1$, $R^3$ and $R^5$ for a compound in each case corresponds to one row of Table A, where $R^1$ is different from $R^3$ Table 16

Compounds of the formula I-A in which n is 1, $R^2$ is 3-fluorine, $R^4$ is methyl and $R^6$ is methoxy and the combination of the radicals $R^1$, $R^3$ and $R^5$ for a compound in each case corresponds to one row of Table A Table 17

Compounds of the formula I-A in which n is 1, $R^2$ is 5-fluorine, $R^4$ is methyl and $R^6$ is methoxy and the combination of the radicals $R^1$, $R^3$ and $R^5$ for a compound in each case corresponds to one row of Table A, where $R^1$ is different from $R^3$ Table 18

Compounds of the formula I-A in which n is 1, $R^2$ is 3-chlorine, $R^4$ is methyl and $R^6$ is methoxy and the combination of the radicals $R^1$, $R^3$ and $R^5$ for a compound in each case corresponds to one row of Table A Table 19

Compounds of the formula I-A in which n is 1, $R^2$ is 5-chlorine, $R^4$ is methyl and $R^6$ is methoxy and the combination of the radicals $R^1$, $R^3$ and $R^5$ for a compound in each case corresponds to one row of Table A, where $R^1$ is different from $R^3$ Table 20

Compounds of the formula I-A in which n is 1, $R^2$ is 3-bromine, $R^4$ is methyl and $R^6$ is methoxy and the combination of the radicals $R^1$, $R^3$ and $R^5$ for a compound in each case corresponds to one row of Table A Table 21

Compounds of the formula I-A in which n is 1, $R^2$ is 5-bromine, $R^4$ is methyl and $R^6$ is methoxy and the combination of the radicals $R^1$, $R^3$ and $R^5$ for a compound in each case corresponds to one row of Table A, where $R^1$ is different from $R^3$ Table 22

Compounds of the formula I-A in which n is 1, $R^2$ is 3-iodine, $R^4$ is methyl and $R^6$ is methoxy and the combination of the radicals $R^1$, $R^3$ and $R^5$ for a compound in each case corresponds to one row of Table A Table 23

Compounds of the formula I-A in which n is 1, $R^2$ is 5-iodine, $R^4$ is methyl and $R^6$ is methoxy and the combination of the radicals $R^1$, $R^3$ and $R^5$ for a compound in each case corresponds to one row of Table A, where $R^1$ is different from $R^3$ Table 24

Compounds of the formula I-A in which n is 0, $R^4$ is ethyl and $R^6$ is methoxy and the combination of the radicals $R^1$, $R^3$ and $R^5$ for a compound in each case corresponds to one row of Table A Table 25

Compounds of the formula I-A in which n is 1, $R^2$ is 3-methyl, $R^4$ is ethyl and $R^6$ is methoxy and the combination of the radicals $R^1$, $R^3$ and $R^5$ for a compound in each case corresponds to one row of Table A Table 26

Compounds of the formula I-A in which n is 1, $R^2$ is 5-methyl, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 27

Compounds of the formula I-A in which n is 1, $R^2$ is 3-trifluoromethyl, $R^4$ is ethyl and $R^6$ is methoxy and the combination of the radicals $R^1$, $R^3$ and $R^5$ for a compound in each case corresponds to one row of Table A Table 28

Compounds of the formula I-A in which n is 1, $R^2$ is 5-trifluoromethyl, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 29

Compounds of the formula I-A in which n is 1, $R^2$ is 3-hydroxy, $R^4$ is ethyl and $R^6$ is methoxy and the combination of the radicals $R^1$, $R^3$ and $R^5$ for a compound in each case corresponds to one row of Table A Table 30

Compounds of the formula I-A in which n is 1, $R^2$ is 5-hydroxy, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 31

Compounds of the formula I-A in which n is 1, $R^2$ is 3-methoxy, $R^4$ is ethyl and $R^6$ is methoxy and the combination of the radicals $R^1$, $R^3$ and $R^5$ for a compound in each case corresponds to one row of Table A Table 32

Compounds of the formula I-A in which n is 1, $R^2$ is 5-methoxy, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 33

Compounds of the formula I-A in which n is 1, $R^2$ is 3-ethoxy, $R^4$ is ethyl and $R^6$ is methoxy and the combination of the radicals $R^1$, $R^3$ and $R^5$ for a compound in each case corresponds to one row of Table A Table 34

Compounds of the formula I-A in which n is 1, $R^2$ is 5-ethoxy, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 35
Compounds of the formula I-A in which n is 1, $R^2$ is 3-difluoromethoxy, $R^4$ is ethyl and $R^6$ is methoxy and the combination of the radicals $R^1$, $R^3$ and $R^5$ for a compound in each case corresponds to one row of Table A Table 36
Compounds of the formula I-A in which n is 1, $R^2$ is 5-difluoromethoxy, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 37
Compounds of the formula I-A in which n is 1, $R^2$ is 3-chlorofluoromethoxy, $R^4$ is ethyl and $R^6$ is methoxy and the combination of the radicals $R^1$, $R^3$ and $R^5$ for a compound in each case corresponds to one row of Table A Table 38
Compounds of the formula I-A in which n is 1, $R^2$ is 5-chlorofluoromethoxy, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 39
Compounds of the formula I-A in which n is 1, $R^2$ is 3-fluorine, $R^4$ is ethyl and $R^6$ is methoxy and the combination of the radicals $R^1$, $R^3$ and $R^5$ for a compound in each case corresponds to one row of Table A Table 40
Compounds of the formula I-A in which n is 1, $R^2$ is 5-fluorine, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 41
Compounds of the formula I-A in which n is 1, $R^2$ is 3-chlorine, $R^4$ is ethyl and $R^6$ is methoxy and the combination of the radicals $R^1$, $R^3$ and $R^5$ for a compound in each case corresponds to one row of Table A Table 42
Compounds of the formula I-A in which n is 1, $R^2$ is 5-chlorine, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 43
Compounds of the formula I-A in which n is 1, $R^2$ is 3-bromine, $R^4$ is ethyl and $R^6$ is methoxy and the combination of the radicals $R^1$, $R^3$ and $R^5$ for a compound in each case corresponds to one row of Table A Table 44
Compounds of the formula I-A in which n is 1, $R^2$ is 5-bromine, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 45
Compounds of the formula I-A in which n is 1, $R^2$ is 3-iodine, $R^4$ is ethyl and $R^6$ is methoxy and the combination of the radicals $R^1$, $R^3$ and $R^5$ for a compound in each case corresponds to one row of Table A Table 46
Compounds of the formula I-A in which n is 1, $R^2$ is 5-iodine, $R^4$ is ethyl and $R^6$ is methoxy and the combination of the radicals $R^1$, $R^3$ and $R^5$ for a compound in each case corresponds to one row of Table A, where $R^1$ is different from $R^3$ Table 47
Compounds of the formula I-A in which n is 0, $R^4$ is trifluoromethyl and $R^6$ is methoxy and the combination of the radicals $R^1$, $R^3$ and $R^5$ for a compound in each case corresponds to one row of Table A Table 48
Compounds of the formula I-A in which n is 1, $R^2$ is 3-methyl, $R^4$ is trifluoromethyl and $R^6$ is methoxy and the combination of the radicals $R^1$, $R^3$ and $R^5$ for a compound in each case corresponds to one row of Table A Table 49
Compounds of the formula I-A in which n is 1, $R^2$ is 5-methyl, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 50
Compounds of the formula I-A in which n is 1, $R^2$ is 3-trifluoromethyl, $R^4$ is trifluoromethyl and $R^6$ is methoxy and the combination of the radicals $R^1$, $R^3$ and $R^5$ for a compound in each case corresponds to one row of Table A Table 51
Compounds of the formula I-A in which n is 1, $R^2$ is 5-trifluoromethyl, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 52
Compounds of the formula I-A in which n is 1, $R^2$ is 3-hydroxyl, $R^4$ is trifluoromethyl and $R^6$ is methoxy and the combination of the radicals $R^1$, $R^3$ and $R^5$ for a compound in each case corresponds to one row of Table A Table 53
Compounds of the formula I-A in which n is 1, $R^2$ is 5-hydroxy, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 54
Compounds of the formula I-A in which n is 1, $R^2$ is 3-methoxy, $R^4$ is trifluoromethyl and $R^6$ is methoxy and the combination of the radicals $R^1$, $R^3$ and $R^5$ for a compound in each case corresponds to one row of Table A Table 55
Compounds of the formula I-A in which n is 1, $R^2$ is 5-methoxy, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 56
Compounds of the formula I-A in which n is 1, $R^2$ is 3-ethoxy, $R^4$ is trifluoromethyl and $R^6$ is methoxy and the combination of the radicals $R^1$, $R^3$ and $R^5$ for a compound in each case corresponds to one row of Table A Table 57
Compounds of the formula I-A in which n is 1, $R^2$ is 5-ethoxy, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 58
Compounds of the formula I-A in which n is 1, $R^2$ is 3-difluoromethoxy, $R^4$ is trifluoromethyl and $R^6$ is methoxy and the combination of the radicals $R^1$, $R^3$ and $R^5$ for a compound in each case corresponds to one row of Table A Table 59
Compounds of the formula I-A in which n is 1, $R^2$ is 5-difluoromethoxy, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 60
Compounds of the formula I-A in which n is 1, $R^2$ is 3-chlorofluoromethoxy, $R^4$ is trifluoromethyl and $R^6$ is methoxy and the combination of the radicals $R^1$, $R^3$ and $R^5$ for a compound in each case corresponds to one row of Table A Table 61
Compounds of the formula I-A in which n is 1, $R^2$ is 5-chlorofluoromethoxy, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 62
Compounds of the formula I-A in which n is 1, $R^2$ is 3-fluorine, $R^4$ is trifluoromethyl and $R^6$ is methoxy and the combination of the radicals $R^1$, $R^3$ and $R^5$ for a compound in each case corresponds to one row of Table A Table 63
Compounds of the formula I-A in which n is 1, $R^2$ is 5-fluorine, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 64
Compounds of the formula I-A in which n is 1, $R^2$ is 3-chlorine, $R^4$ is trifluoromethyl and $R^6$ is methoxy and the combination of the radicals $R^1$, $R^3$ and $R^5$ for a compound in each case corresponds to one row of Table A Table 65
Compounds of the formula I-A in which n is 1, $R^2$ is 5-chlorine, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 66
Compounds of the formula I-A in which n is 1, $R^2$ is 3-bromine, $R^4$ is trifluoromethyl and $R^6$ is methoxy and the combination of the radicals $R^1$, $R^3$ and $R^5$ for a compound in each case corresponds to one row of Table A Table 67
Compounds of the formula I-A in which n is 1, $R^2$ is 5-bromine, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 68
Compounds of the formula I-A in which n is 1, $R^2$ is 3-iodine, $R^4$ is trifluoromethyl and $R^6$ is methoxy and the combination of the radicals $R^1$, $R^3$ and $R^5$ for a compound in each case corresponds to one row of Table A Table 69
Compounds of the formula I-A in which n is 1, $R^2$ is 5-iodine, $R^4$ is trifluoromethyl and $R^6$ is methoxy and the combination of the radicals $R^1$, $R^3$ and $R^5$ for a compound in each case corresponds to one row of Table A, where $R^1$ is different from $R^3$ Table 70
Compounds of the formula I-A in which n is 0, $R^4$ is methyl and $R^6$ is ethoxy and the combination of the radicals $R^1$, $R^3$ and $R^5$ for a compound in each case corresponds to one row of Table A Table 71
Compounds of the formula I-A in which n is 1, $R^2$ is 3-methyl, $R^4$ is methyl and $R^6$ is ethoxy and the combination of the radicals $R^1$, $R^3$ and $R^5$ for a compound in each case corresponds to one row of Table A Table 72
Compounds of the formula I-A in which n is 1, $R^2$ is 5-methyl, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 73
Compounds of the formula I-A in which n is 1, $R^2$ is 3-trifluoromethyl, $R^4$ is methyl and $R^6$ is ethoxy and the combination of the radicals $R^1$, $R^3$ and $R^5$ for a compound in each case corresponds to one row of Table A Table 74
Compounds of the formula I-A in which n is 1, $R^2$ is 5-trifluoromethyl, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 75
Compounds of the formula I-A in which n is 1, $R^2$ is 3-hydroxyl, $R^4$ is methyl and $R^6$ is ethoxy and the combination of the radicals $R^1$, $R^3$ and $R^5$ for a compound in each case corresponds to one row of Table A Table 76
Compounds of the formula I-A in which n is 1, $R^2$ is 5-hydroxyl, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 77
Compounds of the formula I-A in which n is 1, $R^2$ is 3-methoxy, $R^4$ is methyl and $R^6$ is ethoxy and the combination of the radicals $R^1$, $R^3$ and $R^5$ for a compound in each case corresponds to one row of Table A Table 78
Compounds of the formula I-A in which n is 1, $R^2$ is 5-methoxy, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 79
Compounds of the formula I-A in which n is 1, $R^2$ is 3-ethoxy, $R^4$ is methyl and $R^6$ is ethoxy and the combination of the radicals $R^1$, $R^3$ and $R^5$ for a compound in each case corresponds to one row of Table A Table 80
Compounds of the formula I-A in which n is 1, $R^2$ is 5-ethoxy, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 81
Compounds of the formula I-A in which n is 1, $R^2$ is 3-difluoromethoxy, $R^4$ is methyl and $R^6$ is ethoxy and the combination of the radicals $R^1$, $R^3$ and $R^5$ for a compound in each case corresponds to one row of Table A Table 82
Compounds of the formula I-A in which n is 1, $R^2$ is 5-difluoromethoxy, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 83
Compounds of the formula I-A in which n is 1, $R^2$ is 3-chlorofluoromethoxy, $R^4$ is methyl and $R^6$ is ethoxy and the combination of the radicals $R^1$, $R^3$ and $R^5$ for a compound in each case corresponds to one row of Table A Table 84
Compounds of the formula I-A in which n is 1, $R^2$ is 5-chlorofluoromethoxy, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 85
Compounds of the formula I-A in which n is 1, $R^2$ is 3-fluorine, $R^4$ is methyl and $R^6$ is ethoxy and the combination of the radicals $R^1$, $R^3$ and $R^5$ for a compound in each case corresponds to one row of Table A Table 86
Compounds of the formula I-A in which n is 1, $R^2$ is 5-fluorine, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 87
Compounds of the formula I-A in which n is 1, $R^2$ is 3-chlorine, $R^4$ is methyl and $R^6$ is ethoxy and the combination of the radicals $R^1$, $R^3$ and $R^5$ for a compound in each case corresponds to one row of Table A Table 88
Compounds of the formula I-A in which n is 1, $R^2$ is 5-chlorine, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 89
Compounds of the formula I-A in which n is 1, $R^2$ is 3-bromine, $R^4$ is methyl and $R^6$ is ethoxy and the combination of the radicals $R^1$, $R^3$ and $R^5$ for a compound in each case corresponds to one row of Table A Table 90
Compounds of the formula I-A in which n is 1, $R^2$ is 5-bromine, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 91
Compounds of the formula I-A in which n is 1, $R^2$ is 3-iodine, $R^4$ is methyl and $R^6$ is ethoxy and the combination of the radicals $R^1$, $R^3$ and $R^5$ for a compound in each case corresponds to one row of Table A Table 92
Compounds of the formula I-A in which n is 1, $R^2$ is 5-iodine, $R^4$ is methyl and $R^6$ is ethoxy and the combination of the radicals $R^1$, $R^3$ and $R^5$ for a compound in each case corresponds to one row of Table A, where $R^1$ is different from $R^3$ Table 93
Compounds of the formula I-A in which n is 0, $R^4$ is ethyl and $R^6$ is ethoxy and the combination of the radicals $R^1$, $R^3$ and $R^5$ for a compound in each case corresponds to one row of Table A Table 94
Compounds of the formula I-A in which n is 1, $R^2$ is 3-methyl, $R^4$ is ethyl and $R^6$ is ethoxy and the combination of the radicals $R^1$, $R^3$ and $R^5$ for a compound in each case corresponds to one row of Table A Table 95
Compounds of the formula I-A in which n is 1, $R^2$ is 5-methyl, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 96
Compounds of the formula I-A in which n is 1, $R^2$ is 3-trifluoromethyl, $R^4$ is ethyl and $R^6$ is ethoxy and the combination of the radicals $R^1$, $R^3$ and $R^5$ for a compound in each case corresponds to one row of Table A Table 97
Compounds of the formula I-A in which n is 1, $R^2$ is 5-trifluoromethoxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 98
Compounds of the formula I-A in which n is 1, $R^2$ is 3-hydroxy, $R^4$ is ethyl and $R^6$ is ethoxy and the combination of the radicals $R^1$, $R^3$ and $R^5$ for a compound in each case corresponds to one row of Table A Table 99
Compounds of the formula I-A in which n is 1, $R^2$ is 5-hydroxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 100
Compounds of the formula I-A in which n is 1, $R^2$ is 3-methoxy, $R^4$ is ethyl and $R^6$ is ethoxy and the combination of the radicals $R^1$, $R^3$ and $R^5$ for a compound in each case corresponds to one row of Table A Table 101
Compounds of the formula I-A in which n is 1, $R^2$ is 5-methoxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 102
Compounds of the formula I-A in which n is 1, $R^2$ is 3-ethoxy, $R^4$ is ethyl and $R^6$ is ethoxy and the combination of the radicals $R^1$, $R^3$ and $R^5$ for a compound in each case corresponds to one row of Table A Table 103
Compounds of the formula I-A in which n is 1, $R^2$ is 5-ethoxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 104
Compounds of the formula I-A in which n is 1, $R^2$ is 3-difluoromethoxy, $R^4$ is ethyl and $R^6$ is ethoxy and the combination of the radicals $R^1$, $R^3$ and $R^5$ for a compound in each case corresponds to one row of Table A Table 105
Compounds of the formula I-A in which n is 1, $R^2$ is 5-difluoromethoxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 106
Compounds of the formula I-A in which n is 1, $R^2$ is 3-chlorofluoromethoxy, $R^4$ is ethyl and $R^6$ is ethoxy and the combination of the radicals $R^1$, $R^3$ and $R^5$ for a compound in each case corresponds to one row of Table A Table 107
Compounds of the formula I-A in which n is 1, $R^2$ is 5-chlorofluoromethoxy, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 108
Compounds of the formula I-A in which n is 1, $R^2$ is 3-fluorine, $R^4$ is ethyl and $R^6$ is ethoxy and the combination of the radicals $R^1$, $R^3$ and $R^5$ for a compound in each case corresponds to one row of Table A Table 109
Compounds of the formula I-A in which n is 1, $R^2$ is 5-fluorine, $R^4$ is ethyl and $R^6$ is ethoxy and the combination of the radicals $R^1$, $R^3$ and $R^5$ for a compound in each case corresponds to one row of 35 Table A, where $R^1$ is different from $R^3$ Table 110
Compounds of the formula I-A in which n is 1, $R^2$ is 3-chlorine, $R^4$ is ethyl and $R^6$ is ethoxy and the combination of the radicals $R^1$, $R^3$ and $R^5$ for a compound in each case corresponds to one row of Table A Table 111
Compounds of the formula I-A in which n is 1, $R^2$ is 5-chlorine, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 112
Compounds of the formula I-A in which n is 1, $R^2$ is 3-bromine, $R^4$ is ethyl and $R^6$ is ethoxy and the combination of the radicals $R^1$, $R^3$ and $R^5$ for a compound in each case corresponds to one row of Table A Table 113
Compounds of the formula I-A in which n is 1, $R^2$ is 5-bromine, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 114
Compounds of the formula I-A in which n is 1, $R^2$ is 3-iodine, $R^4$ is ethyl and $R^6$ is ethoxy and the combination of the radicals $R^1$, $R^3$ and $R^5$ for a compound in each case corresponds to one row of Table A Table 115
Compounds of the formula I-A in which n is 1, $R^2$ is 5-iodine, $R^4$ is ethyl and $R^6$ is ethoxy and the combination of the radicals $R^1$, $R^3$ and $R^5$ for a compound in each case corresponds to one row of Table A, where $R^1$ is different from $R^3$ Table 116
Compounds of the formula I-A in which n is 0, $R^4$ is trifluoromethyl and $R^6$ is ethoxy and the combination of the radicals $R^1$, $R^3$ and $R^5$ for a compound in each case corresponds to one row of Table A Table 117
Compounds of the formula I-A in which n is 1, $R^2$ is 3-methyl, $R^4$ is trifluoromethyl and $R^6$ is ethoxy and the combination of the radicals $R^1$, $R^3$ and $R^5$ for a compound in each case corresponds to one row of Table A Table 118
Compounds of the formula I-A in which n is 1, $R^2$ is 5-methyl, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 119
Compounds of the formula I-A in which n is 1, $R^2$ is 3-trifluoromethyl, $R^4$ is trifluoromethyl and $R^6$ is ethoxy and the combination of the radicals $R^1$, $R^3$ and $R^5$ for a compound in each case corresponds to one row of Table A Table 120
Compounds of the formula I-A in which n is 1, $R^2$ is 5-trifluoromethyl, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 121
Compounds of the formula I-A in which n is 1, $R^2$ is 3-hydroxy, $R^4$ is trifluoromethyl and $R^6$ is ethoxy and the combination of the radicals $R^1$, $R^3$ and $R^5$ for a compound in each case corresponds to one row of Table A Table 122
Compounds of the formula I-A in which n is 1, $R^2$ is 5-hydroxy, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 123
Compounds of the formula I-A in which n is 1, $R^2$ is 3-methoxy, $R^4$ is trifluoromethyl and $R^6$ is ethoxy and the combination of the radicals $R^1$, $R^3$ and $R^5$ for a compound in each case corresponds to one row of Table A Table 124
Compounds of the formula I-A in which n is 1, $R^2$ is 5-methoxy, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 125
Compounds of the formula I-A in which n is 1, $R^2$ is 3-ethoxy, $R^4$ is trifluoromethyl and $R^6$ is ethoxy and the combination of the radicals $R^1$, $R^3$ and $R^5$ for a compound in each case corresponds to one row of Table A Table 126
Compounds of the formula I-A in which n is 1, $R^2$ is 5-ethoxy, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 127
Compounds of the formula I-A in which n is 1, $R^2$ is 3-difluoromethoxy, $R^4$ is trifluoromethyl and $R^6$ is ethoxy and the combination of the radicals $R^1$, $R^3$ and $R^5$ for a compound in each case corresponds to one row of Table A Table 128
Compounds of the formula I-A in which n is 1, $R^2$ is 5-difluoromethoxy, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 129
Compounds of the formula I-A in which n is 1, $R^2$ is 3-chlorofluoromethoxy, $R^4$ is trifluoromethyl and $R^6$ is ethoxy and the combination of the radicals $R^1$, $R^3$ and $R^5$ for a compound in each case corresponds to one row of Table A Table 130
Compounds of the formula I-A in which n is 1, $R^2$ is 5-chlorofluoromethoxy, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 131
Compounds of the formula I-A in which n is 1, $R^2$ is 3-fluorine, $R^4$ is trifluoromethyl and $R^6$ is ethoxy and the combination of the radicals $R^1$, $R^3$ and $R^5$ for a compound in each case corresponds to one row of Table A Table 132
Compounds of the formula I-A in which n is 1, $R^2$ is 5-fluorine, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 133
Compounds of the formula I-A in which n is 1, $R^2$ is 3-chlorine, $R^4$ is trifluoromethyl and $R^6$ is ethoxy and the combination of the radicals $R^1$, $R^3$ and $R^5$ for a compound in each case corresponds to one row of Table A Table 134
Compounds of the formula I-A in which n is 1, $R^2$ is 5-chlorine, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 135
Compounds of the formula I-A in which n is 1, $R^2$ is 3-bromine, $R^4$ is trifluoromethyl and $R^6$ is ethoxy and the combination of the radicals $R^1$, $R^3$ and $R^5$ for a compound in each case corresponds to one row of Table A Table 136
Compounds of the formula I-A in which n is 1, $R^2$ is 5-bromine, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$ Table 137
Compounds of the formula I-A in which n is 1, $R^2$ is 3-iodine, $R^4$ is trifluoromethyl and $R^6$ is ethoxy and the combination of the radicals $R^1$, $R^3$ and $R^5$ for a compound in each case corresponds to one row of Table A Table 138

Compounds of the formula I-A in which n is 1, $R^2$ is 5-iodine, $R^4$ is trifluoromethyl and $R^6$ is ethoxy and the combination of the radicals $R^1$, $R^3$ and $R^5$ for a compound in each case corresponds to one row of Table A, where $R^1$ is different from $R^3$

TABLE A

| No. | $R^1$ | $R^3$ | $R^5$ |
|---|---|---|---|
| A-1 | CH$_3$ | CH$_3$ | OH |
| A-2 | CH$_2$CH$_3$ | CH$_3$ | OH |
| A-3 | CF$_3$ | CH$_3$ | OH |
| A-4 | F | CH$_3$ | OH |
| A-5 | Cl | CH$_3$ | OH |
| A-6 | Br | CH$_3$ | OH |
| A-7 | I | CH$_3$ | OH |
| A-8 | OH | CH$_3$ | OH |
| A-9 | SH | CH$_3$ | OH |
| A-10 | SCH$_3$ | CH$_3$ | OH |
| A-11 | NH$_2$ | CH$_3$ | OH |
| A-12 | OCH$_3$ | CH$_3$ | OH |
| A-13 | OCHF$_2$ | CH$_3$ | OH |
| A-14 | OCHFCl | CH$_3$ | OH |
| A-15 | OCF$_3$ | CH$_3$ | OH |
| A-16 | OC(=O)CH$_3$ | CH$_3$ | OH |
| A-17 | OC(=O)CH$_2$CH$_3$ | CH$_3$ | OH |
| A-18 | CH$_2$CH$_3$ | CH$_2$CH$_3$ | OH |
| A-19 | CF$_3$ | CH$_2$CH$_3$ | OH |
| A-20 | F | CH$_2$CH$_3$ | OH |
| A-21 | Cl | CH$_2$CH$_3$ | OH |
| A-22 | Br | CH$_2$CH$_3$ | OH |
| A-23 | I | CH$_2$CH$_3$ | OH |
| A-24 | OH | CH$_2$CH$_3$ | OH |
| A-25 | SH | CH$_2$CH$_3$ | OH |
| A-26 | SCH$_3$ | CH$_2$CH$_3$ | OH |
| A-27 | NH$_2$ | CH$_2$CH$_3$ | OH |
| A-28 | OCH$_3$ | CH$_2$CH$_3$ | OH |
| A-29 | OCHF$_2$ | CH$_2$CH$_3$ | OH |
| A-30 | OCHFCl | CH$_2$CH$_3$ | OH |
| A-31 | OCF$_3$ | CH$_2$CH$_3$ | OH |
| A-32 | OC(=O)CH$_3$ | CH$_2$CH$_3$ | OH |
| A-33 | OC(=O)CH$_2$CH$_3$ | CH$_2$CH$_3$ | OH |
| A-34 | CF$_3$ | CF$_3$ | OH |
| A-35 | F | CF$_3$ | OH |
| A-36 | Cl | CF$_3$ | OH |
| A-37 | Br | CF$_3$ | OH |
| A-38 | I | CF$_3$ | OH |
| A-39 | OH | CF$_3$ | OH |
| A-40 | SH | CF$_3$ | OH |
| A-41 | SCH$_3$ | CF$_3$ | OH |
| A-42 | NH$_2$ | CF$_3$ | OH |
| A-43 | OCH$_3$ | CF$_3$ | OH |
| A-44 | OCHF$_2$ | CF$_3$ | OH |
| A-45 | OCHFCl | CF$_3$ | OH |
| A-46 | OCF$_3$ | CF$_3$ | OH |
| A-47 | OC(=O)CH$_3$ | CF$_3$ | OH |
| A-48 | OC(=O)CH$_2$CH$_3$ | CF$_3$ | OH |
| A-49 | F | F | OH |
| A-50 | Cl | F | OH |
| A-51 | Br | F | OH |
| A-52 | I | F | OH |
| A-53 | OH | F | OH |
| A-54 | SH | F | OH |
| A-55 | SCH$_3$ | F | OH |
| A-56 | NH$_2$ | F | OH |
| A-57 | OCH$_3$ | F | OH |
| A-58 | OCHF$_2$ | F | OH |
| A-59 | OCHFCl | F | OH |
| A-60 | OCF$_3$ | F | OH |
| A-61 | OC(=O)CH$_3$ | F | OH |
| A-62 | OC(=O)CH$_2$CH$_3$ | F | OH |
| A-63 | Cl | Cl | OH |
| A-64 | Br | Cl | OH |
| A-65 | I | Cl | OH |
| A-66 | OH | Cl | OH |
| A-67 | SH | Cl | OH |
| A-68 | SCH$_3$ | Cl | OH |
| A-69 | NH$_2$ | Cl | OH |
| A-70 | OCH$_3$ | Cl | OH |
| A-71 | OCHF$_2$ | Cl | OH |
| A-72 | OCHFCl | Cl | OH |
| A-73 | OCF$_3$ | Cl | OH |
| A-74 | OC(=O)CH$_3$ | Cl | OH |
| A-75 | OC(=O)CH$_2$CH$_3$ | Cl | OH |
| A-76 | Br | Br | OH |
| A-77 | I | Br | OH |
| A-78 | OH | Br | OH |
| A-79 | SH | Br | OH |
| A-80 | SCH$_3$ | Br | OH |
| A-81 | NH$_2$ | Br | OH |
| A-82 | OCH$_3$ | Br | OH |
| A-83 | OCHF$_2$ | Br | OH |
| A-84 | OCHFCl | Br | OH |
| A-85 | OCF$_3$ | Br | OH |
| A-86 | OC(=O)CH$_3$ | Br | OH |
| A-87 | OC(=O)CH$_2$CH$_3$ | Br | OH |
| A-88 | I | I | OH |
| A-89 | OH | I | OH |
| A-90 | SH | I | OH |
| A-91 | SCH$_3$ | I | OH |
| A-92 | NH$_2$ | I | OH |
| A-93 | OCH$_3$ | I | OH |
| A-94 | OCHF$_2$ | I | OH |
| A-95 | OCHFCl | I | OH |
| A-96 | OCF$_3$ | I | OH |
| A-97 | OC(=O)CH$_3$ | I | OH |
| A-98 | OC(=O)CH$_2$CH$_3$ | I | OH |
| A-99 | OH | OH | OH |
| A-100 | SH | OH | OH |
| A-101 | SCH$_3$ | OH | OH |
| A-102 | NH$_2$ | OH | OH |
| A-103 | OCH$_3$ | OH | OH |
| A-104 | OCHF$_2$ | OH | OH |
| A-105 | OCHFCl | OH | OH |
| A-106 | OCF$_3$ | OH | OH |
| A-107 | OC(=O)CH$_3$ | OH | OH |
| A-108 | OC(=O)CH$_2$CH$_3$ | OH | OH |
| A-109 | SH | SH | OH |
| A-110 | SCH$_3$ | SH | OH |
| A-111 | NH$_2$ | SH | OH |
| A-112 | OCH$_3$ | SH | OH |
| A-113 | OCHF$_2$ | SH | OH |
| A-114 | OCHFCl | SH | OH |
| A-115 | OCF$_3$ | SH | OH |
| A-116 | OC(=O)CH$_3$ | SH | OH |
| A-117 | OC(=O)CH$_2$CH$_3$ | SH | OH |
| A-118 | SCH$_3$ | SCH$_3$ | OH |
| A-119 | NH$_2$ | SCH$_3$ | OH |
| A-120 | OCH$_3$ | SCH$_3$ | OH |
| A-121 | OCHF$_2$ | SCH$_3$ | OH |
| A-122 | OCHFCl | SCH$_3$ | OH |
| A-123 | OCF$_3$ | SCH$_3$ | OH |
| A-124 | OC(=O)CH$_3$ | SCH$_3$ | OH |
| A-125 | OC(=O)CH$_2$CH$_3$ | SCH$_3$ | OH |

TABLE A-continued

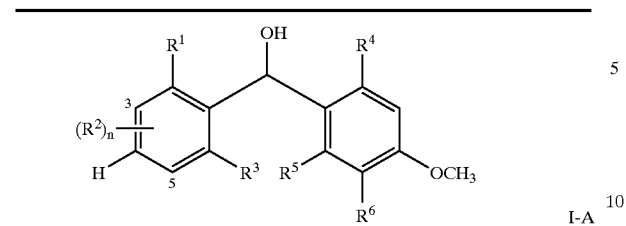

| No. | R¹ | R³ | R⁵ |
|---|---|---|---|
| A-126 | NH₂ | NH₂ | OH |
| A-127 | OCH₃ | NH₂ | OH |
| A-128 | OCHF₂ | NH₂ | OH |
| A-129 | OCHFCl | NH₂ | OH |
| A-130 | OCF₃ | NH₂ | OH |
| A-131 | OC(=O)CH₃ | NH₂ | OH |
| A-132 | OC(=O)CH₂CH₃ | NH₂ | OH |
| A-133 | OCH₃ | OCH₃ | OH |
| A-134 | OCHF₂ | OCH₃ | OH |
| A-135 | OCHFCl | OCH₃ | OH |
| A-136 | OCF₃ | OCH₃ | OH |
| A-137 | OC(=O)CH₃ | OCH₃ | OH |
| A-138 | OC(=O)CH₂CH₃ | OCH₃ | OH |
| A-139 | OCHF₂ | OCHF₂ | OH |
| A-140 | OCHFCl | OCHF₂ | OH |
| A-141 | OCF₃ | OCHF₂ | OH |
| A-142 | OC(=O)CH₃ | OCHF₂ | OH |
| A-143 | OC(=O)CH₂CH₃ | OCHF₂ | OH |
| A-144 | OCHFCl | OCHFCl | OH |
| A-145 | OCF₃ | OCHFCl | OH |
| A-146 | OC(=O)CH₃ | OCHFCl | OH |
| A-147 | OC(=O)CH₂CH₃ | OCHFCl | OH |
| A-148 | OCF₃ | OCF₃ | OH |
| A-149 | OC(=O)CH₃ | OCF₃ | OH |
| A-150 | OC(=O)CH₂CH₃ | OCF₃ | OH |
| A-151 | OC(=O)CH₃ | OC(=O)CH₃ | OH |
| A-152 | OC(=O)CH₂CH₃ | OC(=O)CH₃ | OH |
| A-153 | OC(=O)CH₂CH₃ | OC(=O)CH₂CH₃ | OH |
| A-154 | CH₃ | CH₃ | OCH₃ |
| A-155 | CH₂CH₃ | CH₃ | OCH₃ |
| A-156 | CF₃ | CH₃ | OCH₃ |
| A-157 | F | CH₃ | OCH₃ |
| A-158 | Cl | CH₃ | OCH₃ |
| A-159 | Br | CH₃ | OCH₃ |
| A-160 | I | CH₃ | OCH₃ |
| A-161 | OH | CH₃ | OCH₃ |
| A-162 | SH | CH₃ | OCH₃ |
| A-163 | SCH₃ | CH₃ | OCH₃ |
| A-164 | NH₂ | CH₃ | OCH₃ |
| A-165 | OCH₃ | CH₃ | OCH₃ |
| A-166 | OCHF₂ | CH₃ | OCH₃ |
| A-167 | OCHFCl | CH₃ | OCH₃ |
| A-168 | OCF₃ | CH₃ | OCH₃ |
| A-169 | OC(=O)CH₃ | CH₃ | OCH₃ |
| A-170 | OC(=O)CH₂CH₃ | CH₃ | OCH₃ |
| A-171 | CH₂CH₃ | CH₂CH₃ | OCH₃ |
| A-172 | CF₃ | CH₂CH₃ | OCH₃ |
| A-173 | F | CH₂CH₃ | OCH₃ |
| A-174 | Cl | CH₂CH₃ | OCH₃ |
| A-175 | Br | CH₂CH₃ | OCH₃ |
| A-176 | I | CH₂CH₃ | OCH₃ |
| A-177 | OH | CH₂CH₃ | OCH₃ |
| A-178 | SH | CH₂CH₃ | OCH₃ |
| A-179 | SCH₃ | CH₂CH₃ | OCH₃ |
| A-180 | NH₂ | CH₂CH₃ | OCH₃ |
| A-181 | OCH₃ | CH₂CH₃ | OCH₃ |
| A-182 | OCHF₂ | CH₂CH₃ | OCH₃ |
| A-183 | OCHFCl | CH₂CH₃ | OCH₃ |
| A-184 | OCF₃ | CH₂CH₃ | OCH₃ |
| A-185 | OC(=O)CH₃ | CH₂CH₃ | OCH₃ |
| A-186 | OC(=O)CH₂CH₃ | CH₂CH₃ | OCH₃ |
| A-187 | CF₃ | CF₃ | OCH₃ |
| A-188 | F | CF₃ | OCH₃ |
| A-189 | Cl | CF₃ | OCH₃ |
| A-190 | Br | CF₃ | OCH₃ |
| A-191 | I | CF₃ | OCH₃ |
| A-192 | OH | CF₃ | OCH₃ |
| A-193 | SH | CF₃ | OCH₃ |
| A-194 | SCH₃ | CF₃ | OCH₃ |
| A-195 | NH₂ | CF₃ | OCH₃ |
| A-196 | OCH₃ | CF₃ | OCH₃ |
| A-197 | OCHF₂ | CF₃ | OCH₃ |
| A-198 | OCHFCl | CF₃ | OCH₃ |
| A-199 | OCF₃ | CF₃ | OCH₃ |
| A-200 | OC(=O)CH₃ | CF₃ | OCH₃ |
| A-201 | OC(=O)CH₂CH₃ | CF₃ | OCH₃ |
| A-202 | F | F | OCH₃ |
| A-203 | Cl | F | OCH₃ |
| A-204 | Br | F | OCH₃ |
| A-205 | I | F | OCH₃ |
| A-206 | OH | F | OCH₃ |
| A-207 | SH | F | OCH₃ |
| A-208 | SCH₃ | F | OCH₃ |
| A-209 | NH₂ | F | OCH₃ |
| A-210 | OCH₃ | F | OCH₃ |
| A-211 | OCHF₂ | F | OCH₃ |
| A-212 | OCHFCl | F | OCH₃ |
| A-213 | OCF₃ | F | OCH₃ |
| A-214 | OC(=O)CH₃ | F | OCH₃ |
| A-215 | OC(=O)CH₂CH₃ | F | OCH₃ |
| A-216 | Cl | Cl | OCH₃ |
| A-217 | Br | Cl | OCH₃ |
| A-218 | I | Cl | OCH₃ |
| A-219 | OH | Cl | OCH₃ |
| A-220 | SH | Cl | OCH₃ |
| A-221 | SCH₃ | Cl | OCH₃ |
| A-222 | NH₂ | Cl | OCH₃ |
| A-223 | OCH₃ | Cl | OCH₃ |
| A-224 | OCHF₂ | Cl | OCH₃ |
| A-225 | OCHFCl | Cl | OCH₃ |
| A-226 | OCF₃ | Cl | OCH₃ |
| A-227 | OC(=O)CH₃ | Cl | OCH₃ |
| A-228 | OC(=O)CH₂CH₃ | Cl | OCH₃ |
| A-229 | Br | Br | OCH₃ |
| A-230 | I | Br | OCH₃ |
| A-231 | OH | Br | OCH₃ |
| A-232 | SH | Br | OCH₃ |
| A-233 | SCH₃ | Br | OCH₃ |
| A-234 | NH₂ | Br | OCH₃ |
| A-235 | OCH₃ | Br | OCH₃ |
| A-236 | OCHF₂ | Br | OCH₃ |
| A-237 | OCHFCl | Br | OCH₃ |
| A-238 | OCF₃ | Br | OCH₃ |
| A-239 | OC(=O)CH₃ | Br | OCH₃ |
| A-240 | OC(=O)CH₂CH₃ | Br | OCH₃ |
| A-241 | I | I | OCH₃ |
| A-242 | OH | I | OCH₃ |
| A-243 | SH | I | OCH₃ |
| A-244 | SCH₃ | I | OCH₃ |
| A-245 | NH₂ | I | OCH₃ |
| A-246 | OCH₃ | I | OCH₃ |
| A-247 | OCHF₂ | I | OCH₃ |
| A-248 | OCHFCl | I | OCH₃ |
| A-249 | OCF₃ | I | OCH₃ |
| A-250 | OC(=O)CH₃ | I | OCH₃ |
| A-251 | OC(=O)CH₂CH₃ | I | OCH₃ |
| A-252 | OH | OH | OCH₃ |
| A-253 | SH | OH | OCH₃ |
| A-254 | SCH₃ | OH | OCH₃ |
| A-255 | NH₂ | OH | OCH₃ |
| A-256 | OCH₃ | OH | OCH₃ |
| A-257 | OCHF₂ | OH | OCH₃ |

TABLE A-continued

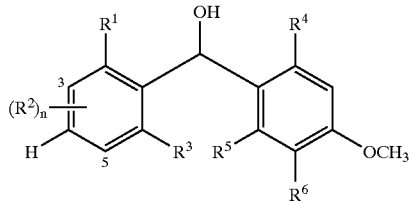

I-A

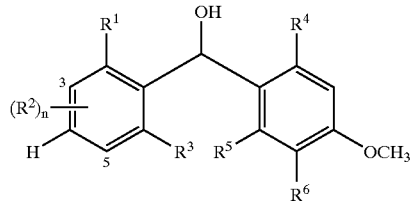

I-A

| No. | R¹ | R³ | R⁵ |
|---|---|---|---|
| A-258 | OCHFCl | OH | OCH$_3$ |
| A-259 | OCF$_3$ | OH | OCH$_3$ |
| A-260 | OC(=O)CH$_3$ | OH | OCH$_3$ |
| A-261 | OC(=O)CH$_2$CH$_3$ | OH | OCH$_3$ |
| A-262 | SH | SH | OCH$_3$ |
| A-263 | SCH$_3$ | SH | OCH$_3$ |
| A-264 | NH$_2$ | SH | OCH$_3$ |
| A-265 | OCH$_3$ | SH | OCH$_3$ |
| A-266 | OCHF$_2$ | SH | OCH$_3$ |
| A-267 | OCHFCl | SH | OCH$_3$ |
| A-268 | OCF$_3$ | SH | OCH$_3$ |
| A-269 | OC(=O)CH$_3$ | SH | OCH$_3$ |
| A-270 | OC(=O)CH$_2$CH$_3$ | SH | OCH$_3$ |
| A-271 | SCH$_3$ | SCH$_3$ | OCH$_3$ |
| A-272 | NH$_2$ | SCH$_3$ | OCH$_3$ |
| A-273 | OCH$_3$ | SCH$_3$ | OCH$_3$ |
| A-274 | OCHF$_2$ | SCH$_3$ | OCH$_3$ |
| A-275 | OCHFCl | SCH$_3$ | OCH$_3$ |
| A-276 | OCF$_3$ | SCH$_3$ | OCH$_3$ |
| A-277 | OC(=O)CH$_3$ | SCH$_3$ | OCH$_3$ |
| A-278 | OC(=O)CH$_2$CH$_3$ | SCH$_3$ | OCH$_3$ |
| A-279 | NH$_2$ | NH$_2$ | OCH$_3$ |
| A-280 | OCH$_3$ | NH$_2$ | OCH$_3$ |
| A-281 | OCHF$_2$ | NH$_2$ | OCH$_3$ |
| A-282 | OCHFCl | NH$_2$ | OCH$_3$ |
| A-283 | OCF$_3$ | NH$_2$ | OCH$_3$ |
| A-284 | OC(=O)CH$_3$ | NH$_2$ | OCH$_3$ |
| A-285 | OC(=O)CH$_2$CH$_3$ | NH$_2$ | OCH$_3$ |
| A-286 | OCH$_3$ | OCH$_3$ | OCH$_3$ |
| A-287 | OCHF$_2$ | OCH$_3$ | OCH$_3$ |
| A-288 | OCHFCl | OCH$_3$ | OCH$_3$ |
| A-289 | OCF$_3$ | OCH$_3$ | OCH$_3$ |
| A-290 | OC(=O)CH$_3$ | OCH$_3$ | OCH$_3$ |
| A-291 | OC(=O)CH$_2$CH$_3$ | OCH$_3$ | OCH$_3$ |
| A-292 | OCHF$_2$ | OCHF$_2$ | OCH$_3$ |
| A-293 | OCHFCl | OCHF$_2$ | OCH$_3$ |
| A-294 | OCF$_3$ | OCHF$_2$ | OCH$_3$ |
| A-295 | OC(=O)CH$_3$ | OCHF$_2$ | OCH$_3$ |
| A-296 | OC(=O)CH$_2$CH$_3$ | OCHF$_2$ | OCH$_3$ |
| A-297 | OCHFCl | OCHFCl | OCH$_3$ |
| A-298 | OCF$_3$ | OCHFCl | OCH$_3$ |
| A-299 | OC(=O)CH$_3$ | OCHFCl | OCH$_3$ |
| A-300 | OC(=O)CH$_2$CH$_3$ | OCHFCl | OCH$_3$ |
| A-301 | OCF$_3$ | OCF$_3$ | OCH$_3$ |
| A-302 | OC(=O)CH$_3$ | OCF$_3$ | OCH$_3$ |
| A-303 | OC(=O)CH$_2$CH$_3$ | OCF$_3$ | OCH$_3$ |
| A-304 | OC(=O)CH$_3$ | OC(=O)CH$_3$ | OCH$_3$ |
| A-305 | OC(=O)CH$_2$CH$_3$ | OC(=O)CH$_3$ | OCH$_3$ |
| A-306 | OC(=O)CH$_2$CH$_3$ | OC(=O)CH$_2$CH$_3$ | OCH$_3$ |
| A-307 | CH$_3$ | CH$_3$ | OCH$_2$CH$_3$ |
| A-308 | CH$_2$CH$_3$ | CH$_3$ | OCH$_2$CH$_3$ |
| A-309 | CF$_3$ | CH$_3$ | OCH$_2$CH$_3$ |
| A-310 | F | CH$_3$ | OCH$_2$CH$_3$ |
| A-311 | Cl | CH$_3$ | OCH$_2$CH$_3$ |
| A-312 | Br | CH$_3$ | OCH$_2$CH$_3$ |
| A-313 | I | CH$_3$ | OCH$_2$CH$_3$ |
| A-314 | OH | CH$_3$ | OCH$_2$CH$_3$ |
| A-315 | SH | CH$_3$ | OCH$_2$CH$_3$ |
| A-316 | SCH$_3$ | CH$_3$ | OCH$_2$CH$_3$ |
| A-317 | NH$_2$ | CH$_3$ | OCH$_2$CH$_3$ |
| A-318 | OCH$_3$ | CH$_3$ | OCH$_2$CH$_3$ |
| A-319 | OCHF$_2$ | CH$_3$ | OCH$_2$CH$_3$ |
| A-320 | OCHFCl | CH$_3$ | OCH$_2$CH$_3$ |
| A-321 | OCF$_3$ | CH$_3$ | OCH$_2$CH$_3$ |
| A-322 | OC(=O)CH$_3$ | CH$_3$ | OCH$_2$CH$_3$ |
| A-323 | OC(=O)CH$_2$CH$_3$ | CH$_3$ | OCH$_2$CH$_3$ |
| A-324 | CH$_2$CH$_3$ | CH$_2$CH$_3$ | OCH$_2$CH$_3$ |
| A-325 | CF$_3$ | CH$_2$CH$_3$ | OCH$_2$CH$_3$ |
| A-326 | F | CH$_2$CH$_3$ | OCH$_2$CH$_3$ |
| A-327 | Cl | CH$_2$CH$_3$ | OCH$_2$CH$_3$ |
| A-328 | Br | CH$_2$CH$_3$ | OCH$_2$CH$_3$ |
| A-329 | I | CH$_2$CH$_3$ | OCH$_2$CH$_3$ |
| A-330 | OH | CH$_2$CH$_3$ | OCH$_2$CH$_3$ |
| A-331 | SH | CH$_2$CH$_3$ | OCH$_2$CH$_3$ |
| A-332 | SCH$_3$ | CH$_2$CH$_3$ | OCH$_2$CH$_3$ |
| A-333 | NH$_2$ | CH$_2$CH$_3$ | OCH$_2$CH$_3$ |
| A-334 | OCH$_3$ | CH$_2$CH$_3$ | OCH$_2$CH$_3$ |
| A-335 | OCHF$_2$ | CH$_2$CH$_3$ | OCH$_2$CH$_3$ |
| A-336 | OCHFCl | CH$_2$CH$_3$ | OCH$_2$CH$_3$ |
| A-337 | OCF$_3$ | CH$_2$CH$_3$ | OCH$_2$CH$_3$ |
| A-338 | OC(=O)CH$_3$ | CH$_2$CH$_3$ | OCH$_2$CH$_3$ |
| A-339 | OC(=O)CH$_2$CH$_3$ | CH$_2$CH$_3$ | OCH$_2$CH$_3$ |
| A-340 | CF$_3$ | CF$_3$ | OCH$_2$CH$_3$ |
| A-341 | F | CF$_3$ | OCH$_2$CH$_3$ |
| A-342 | Cl | CF$_3$ | OCH$_2$CH$_3$ |
| A-343 | Br | CF$_3$ | OCH$_2$CH$_3$ |
| A-344 | I | CF$_3$ | OCH$_2$CH$_3$ |
| A-345 | OH | CF$_3$ | OCH$_2$CH$_3$ |
| A-346 | SH | CF$_3$ | OCH$_2$CH$_3$ |
| A-347 | SCH$_3$ | CF$_3$ | OCH$_2$CH$_3$ |
| A-348 | NH$_2$ | CF$_3$ | OCH$_2$CH$_3$ |
| A-349 | OCH$_3$ | CF$_3$ | OCH$_2$CH$_3$ |
| A-350 | OCHF$_2$ | CF$_3$ | OCH$_2$CH$_3$ |
| A-351 | OCHFCl | CF$_3$ | OCH$_2$CH$_3$ |
| A-352 | OCF$_3$ | CF$_3$ | OCH$_2$CH$_3$ |
| A-353 | OC(=O)CH$_3$ | CF$_3$ | OCH$_2$CH$_3$ |
| A-354 | OC(=O)CH$_2$CH$_3$ | CF$_3$ | OCH$_2$CH$_3$ |
| A-355 | F | F | OCH$_2$CH$_3$ |
| A-356 | Cl | F | OCH$_2$CH$_3$ |
| A-357 | Br | F | OCH$_2$CH$_3$ |
| A-358 | I | F | OCH$_2$CH$_3$ |
| A-359 | OH | F | OCH$_2$CH$_3$ |
| A-360 | SH | F | OCH$_2$CH$_3$ |
| A-361 | SCH$_3$ | F | OCH$_2$CH$_3$ |
| A-362 | NH$_2$ | F | OCH$_2$CH$_3$ |
| A-363 | OCH$_3$ | F | OCH$_2$CH$_3$ |
| A-364 | OCHF$_2$ | F | OCH$_2$CH$_3$ |
| A-365 | OCHFCl | F | OCH$_2$CH$_3$ |
| A-366 | OCF$_3$ | F | OCH$_2$CH$_3$ |
| A-367 | OC(=O)CH$_3$ | F | OCH$_2$CH$_3$ |
| A-368 | OC(=O)CH$_2$CH$_3$ | F | OCH$_2$CH$_3$ |
| A-369 | Cl | Cl | OCH$_2$CH$_3$ |
| A-370 | Br | Cl | OCH$_2$CH$_3$ |
| A-371 | I | Cl | OCH$_2$CH$_3$ |
| A-372 | OH | Cl | OCH$_2$CH$_3$ |
| A-373 | SH | Cl | OCH$_2$CH$_3$ |
| A-374 | SCH$_3$ | Cl | OCH$_2$CH$_3$ |
| A-375 | NH$_2$ | Cl | OCH$_2$CH$_3$ |
| A-376 | OCH$_3$ | Cl | OCH$_2$CH$_3$ |
| A-377 | OCHF$_2$ | Cl | OCH$_2$CH$_3$ |
| A-378 | OCHFCl | Cl | OCH$_2$CH$_3$ |
| A-379 | OCF$_3$ | Cl | OCH$_2$CH$_3$ |
| A-380 | OC(=O)CH$_3$ | Cl | OCH$_2$CH$_3$ |
| A-381 | OC(=O)CH$_2$CH$_3$ | Cl | OCH$_2$CH$_3$ |
| A-382 | Br | Br | OCH$_2$CH$_3$ |
| A-383 | I | Br | OCH$_2$CH$_3$ |
| A-384 | OH | Br | OCH$_2$CH$_3$ |
| A-385 | SH | Br | OCH$_2$CH$_3$ |
| A-386 | SCH$_3$ | Br | OCH$_2$CH$_3$ |
| A-387 | NH$_2$ | Br | OCH$_2$CH$_3$ |
| A-388 | OCH$_3$ | Br | OCH$_2$CH$_3$ |
| A-389 | OCHF$_2$ | Br | OCH$_2$CH$_3$ |

TABLE A-continued

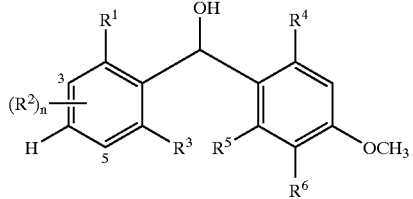

I-A

| No. | R¹ | R³ | R⁵ |
|---|---|---|---|
| A-390 | OCHFCl | Br | OCH₂CH₃ |
| A-391 | OCF₃ | Br | OCH₂CH₃ |
| A-392 | OC(=O)CH₃ | Br | OCH₂CH₃ |
| A-393 | OC(=O)CH₂CH₃ | Br | OCH₂CH₃ |
| A-394 | I | I | OCH₂CH₃ |
| A-395 | OH | I | OCH₂CH₃ |
| A-396 | SH | I | OCH₂CH₃ |
| A-397 | SCH₃ | I | OCH₂CH₃ |
| A-398 | NH₂ | I | OCH₂CH₃ |
| A-399 | OCH₃ | I | OCH₂CH₃ |
| A-400 | OCHF₂ | I | OCH₂CH₃ |
| A-401 | OCHFCl | I | OCH₂CH₃ |
| A-402 | OCF₃ | I | OCH₂CH₃ |
| A-403 | OC(=O)CH₃ | I | OCH₂CH₃ |
| A-404 | OC(=O)CH₂CH₃ | I | OCH₂CH₃ |
| A-405 | OH | OH | OCH₂CH₃ |
| A-406 | SH | OH | OCH₂CH₃ |
| A-407 | SCH₃ | OH | OCH₂CH₃ |
| A-408 | NH₂ | OH | OCH₂CH₃ |
| A-409 | OCH₃ | OH | OCH₂CH₃ |
| A-410 | OCHF₂ | OH | OCH₂CH₃ |
| A-411 | OCHFCl | OH | OCH₂CH₃ |
| A-412 | OCF₃ | OH | OCH₂CH₃ |
| A-413 | OC(=O)CH₃ | OH | OCH₂CH₃ |
| A-414 | OC(=O)CH₂CH₃ | OH | OCH₂CH₃ |
| A-415 | SH | SH | OCH₂CH₃ |
| A-416 | SCH₃ | SH | OCH₂CH₃ |
| A-417 | NH₂ | SH | OCH₂CH₃ |
| A-418 | OCH₃ | SH | OCH₂CH₃ |
| A-419 | OCHF₂ | SH | OCH₂CH₃ |
| A-420 | OCHFCl | SH | OCH₂CH₃ |
| A-421 | OCF₃ | SH | OCH₂CH₃ |
| A-422 | OC(=O)CH₃ | SH | OCH₂CH₃ |
| A-423 | OC(=O)CH₂CH₃ | SH | OCH₂CH₃ |
| A-424 | SCH₃ | SCH₃ | OCH₂CH₃ |
| A-425 | NH₂ | SCH₃ | OCH₂CH₃ |
| A-426 | OCH₃ | SCH₃ | OCH₂CH₃ |
| A-427 | OCHF₂ | SCH₃ | OCH₂CH₃ |
| A-428 | OCHFCl | SCH₃ | OCH₂CH₃ |
| A-429 | OCF₃ | SCH₃ | OCH₂CH₃ |
| A-430 | OC(=O)CH₃ | SCH₃ | OCH₂CH₃ |
| A-431 | OC(=O)CH₂CH₃ | SCH₃ | OCH₂CH₃ |
| A-432 | NH₂ | NH₂ | OCH₂CH₃ |
| A-433 | OCH₃ | NH₂ | OCH₂CH₃ |
| A-434 | OCHF₂ | NH₂ | OCH₂CH₃ |
| A-435 | OCHFCl | NH₂ | OCH₂CH₃ |
| A-436 | OCF₃ | NH₂ | OCH₂CH₃ |
| A-437 | OC(=O)CH₃ | NH₂ | OCH₂CH₃ |
| A-438 | OC(=O)CH₂CH₃ | NH₂ | OCH₂CH₃ |
| A-439 | OCH₃ | OCH₃ | OCH₂CH₃ |
| A-440 | OCHF₂ | OCH₃ | OCH₂CH₃ |
| A-441 | OCHFCl | OCH₃ | OCH₂CH₃ |
| A-442 | OCF₃ | OCH₃ | OCH₂CH₃ |
| A-443 | OC(=O)CH₃ | OCH₃ | OCH₂CH₃ |
| A-444 | OC(=O)CH₂CH₃ | OCH₃ | OCH₂CH₃ |
| A-445 | OCHF₂ | OCHF₂ | OCH₂CH₃ |
| A-446 | OCHFCl | OCHF₂ | OCH₂CH₃ |
| A-447 | OCF₃ | OCHF₂ | OCH₂CH₃ |
| A-448 | OC(=O)CH₃ | OCHF₂ | OCH₂CH₃ |
| A-449 | OC(=O)CH₂CH₃ | OCHF₂ | OCH₂CH₃ |
| A-450 | OCHFCl | OCHFCl | OCH₂CH₃ |
| A-451 | OCF₃ | OCHFCl | OCH₂CH₃ |
| A-452 | OC(=O)CH₃ | OCHFCl | OCH₂CH₃ |
| A-453 | OC(=O)CH₂CH₃ | OCHFCl | OCH₂CH₃ |
| A-454 | OCF₃ | OCF₃ | OCH₂CH₃ |
| A-455 | OC(=O)CH₃ | OCF₃ | OCH₂CH₃ |

TABLE A-continued

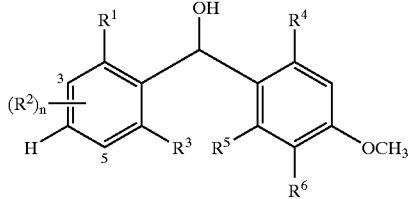

I-A

| No. | R¹ | R³ | R⁵ |
|---|---|---|---|
| A-456 | OC(=O)CH₂CH₃ | OCF₃ | OCH₂CH₃ |
| A-457 | OC(=O)CH₃ | OC(=O)CH₃ | OCH₂CH₃ |
| A-458 | OC(=O)CH₂CH₃ | OC(=O)CH₃ | OCH₂CH₃ |
| A-459 | OC(=O)CH₂CH₃ | OC(=O)CH₂CH₃ | OCH₂CH₃ |
| A-460 | CH₃ | CH₃ | OCH₂CH₂CH₃ |
| A-461 | CH₂CH₃ | CH₃ | OCH₂CH₂CH₃ |
| A-462 | CF₃ | CH₃ | OCH₂CH₂CH₃ |
| A-463 | F | CH₃ | OCH₂CH₂CH₃ |
| A-464 | Cl | CH₃ | OCH₂CH₂CH₃ |
| A-465 | Br | CH₃ | OCH₂CH₂CH₃ |
| A-466 | I | CH₃ | OCH₂CH₂CH₃ |
| A-467 | OH | CH₃ | OCH₂CH₂CH₃ |
| A-468 | SH | CH₃ | OCH₂CH₂CH₃ |
| A-469 | SCH₃ | CH₃ | OCH₂CH₂CH₃ |
| A-470 | NH₂ | CH₃ | OCH₂CH₂CH₃ |
| A-471 | OCH₃ | CH₃ | OCH₂CH₂CH₃ |
| A-472 | OCHF₂ | CH₃ | OCH₂CH₂CH₃ |
| A-473 | OCHFCl | CH₃ | OCH₂CH₂CH₃ |
| A-474 | OCF₃ | CH₃ | OCH₂CH₂CH₃ |
| A-475 | OC(=O)CH₃ | CH₃ | OCH₂CH₂CH₃ |
| A-476 | OC(=O)CH₂CH₃ | CH₃ | OCH₂CH₂CH₃ |
| A-477 | CH₂CH₃ | CH₂CH₃ | OCH₂CH₂CH₃ |
| A-478 | CF₃ | CH₂CH₃ | OCH₂CH₂CH₃ |
| A-479 | F | CH₂CH₃ | OCH₂CH₂CH₃ |
| A-480 | Cl | CH₂CH₃ | OCH₂CH₂CH₃ |
| A-481 | Br | CH₂CH₃ | OCH₂CH₂CH₃ |
| A-482 | I | CH₂CH₃ | OCH₂CH₂CH₃ |
| A-483 | OH | CH₂CH₃ | OCH₂CH₂CH₃ |
| A-484 | SH | CH₂CH₃ | OCH₂CH₂CH₃ |
| A-485 | SCH₃ | CH₂CH₃ | OCH₂CH₂CH₃ |
| A-486 | NH₂ | CH₂CH₃ | OCH₂CH₂CH₃ |
| A-487 | OCH₃ | CH₂CH₃ | OCH₂CH₂CH₃ |
| A-488 | OCHF₂ | CH₂CH₃ | OCH₂CH₂CH₃ |
| A-489 | OCHFCl | CH₂CH₃ | OCH₂CH₂CH₃ |
| A-490 | OCF₃ | CH₂CH₃ | OCH₂CH₂CH₃ |
| A-491 | OC(=O)CH₃ | CH₂CH₃ | OCH₂CH₂CH₃ |
| A-492 | OC(=O)CH₂CH₃ | CH₂CH₃ | OCH₂CH₂CH₃ |
| A-493 | CF₃ | CF₃ | OCH₂CH₂CH₃ |
| A-494 | F | CF₃ | OCH₂CH₂CH₃ |
| A-495 | Cl | CF₃ | OCH₂CH₂CH₃ |
| A-496 | Br | CF₃ | OCH₂CH₂CH₃ |
| A-497 | I | CF₃ | OCH₂CH₂CH₃ |
| A-498 | OH | CF₃ | OCH₂CH₂CH₃ |
| A-499 | SH | CF₃ | OCH₂CH₂CH₃ |
| A-500 | SCH₃ | CF₃ | OCH₂CH₂CH₃ |
| A-501 | NH₂ | CF₃ | OCH₂CH₂CH₃ |
| A-502 | OCH₃ | CF₃ | OCH₂CH₂CH₃ |
| A-503 | OCHF₂ | CF₃ | OCH₂CH₂CH₃ |
| A-504 | OCHFCl | CF₃ | OCH₂CH₂CH₃ |
| A-505 | OCF₃ | CF₃ | OCH₂CH₂CH₃ |
| A-506 | OC(=O)CH₃ | CF₃ | OCH₂CH₂CH₃ |
| A-507 | OC(=O)CH₂CH₃ | CF₃ | OCH₂CH₂CH₃ |
| A-508 | F | F | OCH₂CH₂CH₃ |
| A-509 | Cl | F | OCH₂CH₂CH₃ |
| A-510 | Br | F | OCH₂CH₂CH₃ |
| A-511 | I | F | OCH₂CH₂CH₃ |
| A-512 | OH | F | OCH₂CH₂CH₃ |
| A-513 | SH | F | OCH₂CH₂CH₃ |
| A-514 | SCH₃ | F | OCH₂CH₂CH₃ |
| A-515 | NH₂ | F | OCH₂CH₂CH₃ |
| A-516 | OCH₃ | F | OCH₂CH₂CH₃ |
| A-517 | OCHF₂ | F | OCH₂CH₂CH₃ |
| A-518 | OCHFCl | F | OCH₂CH₂CH₃ |
| A-519 | OCF₃ | F | OCH₂CH₂CH₃ |
| A-520 | OC(=O)CH₃ | F | OCH₂CH₂CH₃ |
| A-521 | OC(=O)CH₂CH₃ | F | OCH₂CH₂CH₃ |

TABLE A-continued

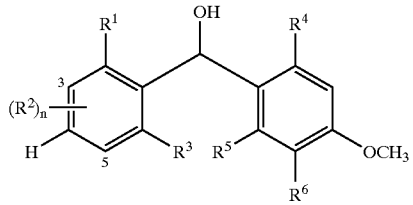

I-A

| No. | R¹ | R³ | R⁵ |
|---|---|---|---|
| A-522 | Cl | Cl | OCH₂CH₂CH₃ |
| A-523 | Br | Cl | OCH₂CH₂CH₃ |
| A-524 | I | Cl | OCH₂CH₂CH₃ |
| A-525 | OH | Cl | OCH₂CH₂CH₃ |
| A-526 | SH | Cl | OCH₂CH₂CH₃ |
| A-527 | SCH₃ | Cl | OCH₂CH₂CH₃ |
| A-528 | NH₂ | Cl | OCH₂CH₂CH₃ |
| A-529 | OCH₃ | Cl | OCH₂CH₂CH₃ |
| A-530 | OCHF₂ | Cl | OCH₂CH₂CH₃ |
| A-531 | OCHFCl | Cl | OCH₂CH₂CH₃ |
| A-532 | OCF₃ | Cl | OCH₂CH₂CH₃ |
| A-533 | OC(=O)CH₃ | Cl | OCH₂CH₂CH₃ |
| A-534 | OC(=O)CH₂CH₃ | Cl | OCH₂CH₂CH₃ |
| A-535 | Br | Br | OCH₂CH₂CH₃ |
| A-536 | I | Br | OCH₂CH₂CH₃ |
| A-537 | OH | Br | OCH₂CH₂CH₃ |
| A-538 | SH | Br | OCH₂CH₂CH₃ |
| A-539 | SCH₃ | Br | OCH₂CH₂CH₃ |
| A-540 | NH₂ | Br | OCH₂CH₂CH₃ |
| A-541 | OCH₃ | Br | OCH₂CH₂CH₃ |
| A-542 | OCHF₂ | Br | OCH₂CH₂CH₃ |
| A-543 | OCHFCl | Br | OCH₂CH₂CH₃ |
| A-544 | OCF₃ | Br | OCH₂CH₂CH₃ |
| A-545 | OC(=O)CH₃ | Br | OCH₂CH₂CH₃ |
| A-546 | OC(=O)CH₂CH₃ | Br | OCH₂CH₂CH₃ |
| A-547 | I | I | OCH₂CH₂CH₃ |
| A-548 | OH | I | OCH₂CH₂CH₃ |
| A-549 | SH | I | OCH₂CH₂CH₃ |
| A-550 | SCH₃ | I | OCH₂CH₂CH₃ |
| A-551 | NH₂ | I | OCH₂CH₂CH₃ |
| A-552 | OCH₃ | I | OCH₂CH₂CH₃ |
| A-553 | OCHF₂ | I | OCH₂CH₂CH₃ |
| A-554 | OCHFCl | I | OCH₂CH₂CH₃ |
| A-555 | OCF₃ | I | OCH₂CH₂CH₃ |
| A-556 | OC(=O)CH₃ | I | OCH₂CH₂CH₃ |
| A-557 | OC(=O)CH₂CH₃ | I | OCH₂CH₂CH₃ |
| A-558 | OH | OH | OCH₂CH₂CH₂ |
| A-559 | SH | OH | OCH₂CH₂CH₃ |
| A-560 | SCH₃ | OH | OCH₂CH₂CH₃ |
| A-561 | NH₂ | OH | OCH₂CH₂CH₃ |
| A-562 | OCH₃ | OH | OCH₂CH₂CH₃ |
| A-563 | OCHF₂ | OH | OCH₂CH₂CH₃ |
| A-564 | OCHFCl | OH | OCH₂CH₂CH₃ |
| A-565 | OCF₃ | OH | OCH₂CH₂CH₃ |
| A-566 | OC(=O)CH₃ | OH | OCH₂CH₂CH₃ |
| A-567 | OC(=O)CH₂CH₃ | OH | OCH₂CH₂CH₃ |
| A-568 | SH | SH | OCH₂CH₂CH₃ |
| A-569 | SCH₃ | SH | OCH₂CH₂CH₃ |
| A-570 | NH₂ | SH | OCH₂CH₂CH₃ |
| A-571 | OCH₃ | SH | OCH₂CH₂CH₃ |
| A-572 | OCHF₂ | SH | OCH₂CH₂CH₃ |
| A-573 | OCHFCl | SH | OCH₂CH₂CH₃ |
| A-574 | OCF₃ | SH | OCH₂CH₂CH₃ |
| A-575 | OC(=O)CH₃ | SH | OCH₂CH₂CH₃ |
| A-576 | OC(=O)CH₂CH₃ | SH | OCH₂CH₂CH₃ |
| A-577 | SCH₃ | SCH₃ | OCH₂CH₂CH₃ |
| A-578 | NH₂ | SCH₃ | OCH₂CH₂CH₃ |
| A-579 | OCH₃ | SCH₃ | OCH₂CH₂CH₃ |
| A-580 | OCHF₂ | SCH₃ | OCH₂CH₂CH₃ |
| A-581 | OCHFCl | SCH₃ | OCH₂CH₂CH₃ |
| A-582 | OCF₃ | SCH₃ | OCH₂CH₂CH₃ |
| A-583 | OC(=O)CH₃ | SCH₃ | OCH₂CH₂CH₃ |
| A-584 | OC(=O)CH₂CH₃ | SCH₃ | OCH₂CH₂CH₃ |
| A-585 | NH₂ | NH₂ | OCH₂CH₂CH₃ |
| A-586 | OCH₃ | NH₂ | OCH₂CH₂CH₃ |
| A-587 | OCHF₂ | NH₂ | OCH₂CH₂CH₃ |
| A-588 | OCHFCl | NH₂ | OCH₂CH₂CH₃ |
| A-589 | OCF₃ | NH₂ | OCH₂CH₂CH₃ |
| A-590 | OC(=O)CH₃ | NH₂ | OCH₂CH₂CH₃ |
| A-591 | OC(=O)CH₂CH₃ | NH₂ | OCH₂CH₂CH₃ |
| A-592 | OCH₃ | OCH₃ | OCH₂CH₂CH₃ |
| A-593 | OCHF₂ | OCH₃ | OCH₂CH₂CH₃ |
| A-594 | OCHFCl | OCH₃ | OCH₂CH₂CH₃ |
| A-595 | OCF₃ | OCH₃ | OCH₂CH₂CH₃ |
| A-596 | OC(=O)CH₃ | OCH₃ | OCH₂CH₂CH₃ |
| A-597 | OC(=O)CH₂CH₃ | OCH₃ | OCH₂CH₂CH₃ |
| A-598 | OCHF₂ | OCHF₂ | OCH₂CH₂CH₃ |
| A-599 | OCHFCl | OCHF₂ | OCH₂CH₂CH₃ |
| A-600 | OCF₃ | OCHF₂ | OCH₂CH₂CH₃ |
| A-601 | OC(=O)CH₃ | OCHF₂ | OCH₂CH₂CH₃ |
| A-602 | OC(=O)CH₂CH₃ | OCHF₂ | OCH₂CH₂CH₃ |
| A-603 | OCHFCl | OCHFCl | OCH₂CH₂CH₃ |
| A-604 | OCF₃ | OCHFCl | OCH₂CH₂CH₃ |
| A-605 | OC(=O)CH₃ | OCHFCl | OCH₂CH₂CH₃ |
| A-606 | OC(=O)CH₂CH₃ | OCHFCl | OCH₂CH₂CH₃ |
| A-607 | OCF₃ | OCF₃ | OCH₂CH₂CH₃ |
| A-608 | OC(=O)CH₃ | OCF₃ | OCH₂CH₂CH₃ |
| A-609 | OC(=O)CH₂CH₃ | OCF₃ | OCH₂CH₂CH₃ |
| A-610 | OC(=O)CH₃ | OC(=O)CH₃ | OCH₂CH₂CH₃ |
| A-611 | OC(=O)CH₂CH₃ | OC(=O)CH₃ | OCH₂CH₂CH₃ |
| A-612 | OC(=O)CH₂CH₃ | OC(=O)CH₂CH₃ | OCH₂CH₂CH₃ |
| A-613 | CH₃ | CH₃ | OCH(CH₃)₂ |
| A-614 | CH₂CH₃ | CH₃ | OCH(CH₃)₂ |
| A-615 | CF₃ | CH₃ | OCH(CH₃)₂ |
| A-616 | F | CH₃ | OCH(CH₃)₂ |
| A-617 | Cl | CH₃ | OCH(CH₃)₂ |
| A-618 | Br | CH₃ | OCH(CH₃)₂ |
| A-619 | I | CH₃ | OCH(CH₃)₂ |
| A-620 | OH | CH₃ | OCH(CH₃)₂ |
| A-621 | SH | CH₃ | OCH(CH₃)₂ |
| A-622 | SCH₃ | CH₃ | OCH(CH₃)₂ |
| A-623 | NH₂ | CH₃ | OCH(CH₃)₂ |
| A-624 | OCH₃ | CH₃ | OCH(CH₃)₂ |
| A-625 | OCHF₂ | CH₃ | OCH(CH₃)₂ |
| A-626 | OCHFCl | CH₃ | OCH(CH₃)₂ |
| A-627 | OCF₃ | CH₃ | OCH(CH₃)₂ |
| A-628 | OC(=O)CH₃ | CH₃ | OCH(CH₃)₂ |
| A-629 | OC(=O)CH₂CH₃ | CH₃ | OCH(CH₃)₂ |
| A-630 | CH₂CH₃ | CH₂CH₃ | OCH(CH₃)₂ |
| A-631 | CF₃ | CH₂CH₃ | OCH(CH₃)₂ |
| A-632 | F | CH₂CH₃ | OCH(CH₃)₂ |
| A-633 | Cl | CH₂CH₃ | OCH(CH₃)₂ |
| A-634 | Br | CH₂CH₃ | OCH(CH₃)₂ |
| A-635 | I | CH₂CH₃ | OCH(CH₃)₂ |
| A-636 | OH | CH₂CH₃ | OCH(CH₃)₂ |
| A-637 | SH | CH₂CH₃ | OCH(CH₃)₂ |
| A-638 | SCH₃ | CH₂CH₃ | OCH(CH₃)₂ |
| A-639 | NH₂ | CH₂CH₃ | OCH(CH₃)₂ |
| A-640 | OCH₃ | CH₂CH₃ | OCH(CH₃)₂ |
| A-641 | OCHF₂ | CH₂CH₃ | OCH(CH₃)₂ |
| A-642 | OCHFCl | CH₂CH₃ | OCH(CH₃)₂ |
| A-643 | OCF₃ | CH₂CH₃ | OCH(CH₃)₂ |
| A-644 | OC(=O)CH₃ | CH₂CH₃ | OCH(CH₃)₂ |
| A-645 | OC(=O)CH₂CH₃ | CH₂CH₃ | OCH(CH₃)₂ |
| A-646 | CF₃ | CF₃ | OCH(CH₃)₂ |
| A-647 | F | CF₃ | OCH(CH₃)₂ |
| A-648 | Cl | CF₃ | OCH(CH₃)₂ |
| A-649 | Br | CF₃ | OCH(CH₃)₂ |
| A-650 | I | CF₃ | OCH(CH₃)₂ |
| A-651 | OH | CF₃ | OCH(CH₃)₂ |
| A-652 | SH | CF₃ | OCH(CH₃)₂ |
| A-653 | SCH₃ | CF₃ | OCH(CH₃)₂ |

TABLE A-continued

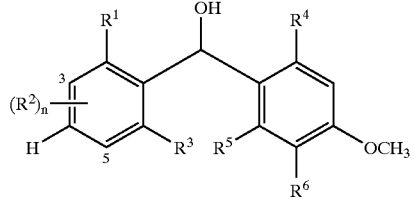

I-A

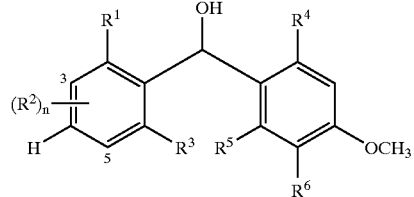

I-A

| No. | R¹ | R³ | R⁵ |
|---|---|---|---|
| A-654 | NH$_2$ | CF$_3$ | OCH(CH$_3$)$_2$ |
| A-655 | OCH$_3$ | CF$_3$ | OCH(CH$_3$)$_2$ |
| A-656 | OCHF$_2$ | CF$_3$ | OCH(CH$_3$)$_2$ |
| A-657 | OCHFCl | CF$_3$ | OCH(CH$_3$)$_2$ |
| A-658 | OCF$_3$ | CF$_3$ | OCH(CH$_3$)$_2$ |
| A-659 | OC(=O)CH$_3$ | CF$_3$ | OCH(CH$_3$)$_2$ |
| A-660 | OC(=O)CH$_2$CH$_3$ | CF$_3$ | OCH(CH$_3$)$_2$ |
| A-661 | F | F | OCH(CH$_3$)$_2$ |
| A-662 | Cl | F | OCH(CH$_3$)$_2$ |
| A-663 | Br | F | OCH(CH$_3$)$_2$ |
| A-664 | I | F | OCH(CH$_3$)$_2$ |
| A-665 | OH | F | OCH(CH$_3$)$_2$ |
| A-666 | SH | F | OCH(CH$_3$)$_2$ |
| A-667 | SCH$_3$ | F | OCH(CH$_3$)$_2$ |
| A-668 | NH$_2$ | F | OCH(CH$_3$)$_2$ |
| A-659 | OCH$_3$ | F | OCH(CH$_3$)$_2$ |
| A-670 | OCHF$_2$ | F | OCH(CH$_3$)$_2$ |
| A-671 | OCHFCl | F | OCH(CH$_3$)$_2$ |
| A-672 | OCF$_3$ | F | OCH(CH$_3$)$_2$ |
| A-673 | OC(=O)CH$_3$ | F | OCH(CH$_3$)$_2$ |
| A-674 | OC(=O)CH$_2$CH$_3$ | F | OCH(CH$_3$)$_2$ |
| A-675 | Cl | Cl | OCH(CH$_3$)$_2$ |
| A-676 | Br | Cl | OCH(CH$_3$)$_2$ |
| A-677 | I | Cl | OCH(CH$_3$)$_2$ |
| A-678 | OH | Cl | OCH(CH$_3$)$_2$ |
| A-679 | SH | Cl | OCH(CH$_3$)$_2$ |
| A-680 | SCH$_3$ | Cl | OCH(CH$_3$)$_2$ |
| A-681 | NH$_2$ | Cl | OCH(CH$_3$)$_2$ |
| A-682 | OCH$_3$ | Cl | OCH(CH$_3$)$_2$ |
| A-683 | OCHF$_2$ | Cl | OCH(CH$_3$)$_2$ |
| A-684 | OCHFCl | Cl | OCH(CH$_3$)$_2$ |
| A-685 | OCF$_3$ | Cl | OCH(CH$_3$)$_2$ |
| A-686 | OC(=O)CH$_3$ | Cl | OCH(CH$_3$)$_2$ |
| A-687 | OC(=O)CH$_2$CH$_3$ | Cl | OCH(CH$_3$)$_2$ |
| A-688 | Br | Br | OCH(CH$_3$)$_2$ |
| A-689 | I | Br | OCH(CH$_3$)$_2$ |
| A-690 | OH | Br | OCH(CH$_3$)$_2$ |
| A-691 | SH | Br | OCH(CH$_3$)$_2$ |
| A-692 | SCH$_3$ | Br | OCH(CH$_3$)$_2$ |
| A-693 | NH$_2$ | Br | OCH(CH$_3$)$_2$ |
| A-694 | OCH$_3$ | Br | OCH(CH$_3$)$_2$ |
| A-695 | OCHF$_2$ | Br | OCH(CH$_3$)$_2$ |
| A-696 | OCHFCl | Br | OCH(CH$_3$)$_2$ |
| A-697 | OCF$_3$ | Br | OCH(CH$_3$)$_2$ |
| A-698 | OC(=O)CH$_3$ | Br | OCH(CH$_3$)$_2$ |
| A-699 | OC(=O)CH$_2$CH$_3$ | Br | OCH(CH$_3$)$_2$ |
| A-700 | I | I | OCH(CH$_3$)$_2$ |
| A-701 | OH | I | OCH(CH$_3$)$_2$ |
| A-702 | SH | I | OCH(CH$_3$)$_2$ |
| A-703 | SCH$_3$ | I | OCH(CH$_3$)$_2$ |
| A-704 | NH$_2$ | I | OCH(CH$_3$)$_2$ |
| A-705 | OCH$_3$ | I | OCH(CH$_3$)$_2$ |
| A-706 | OCHF$_2$ | I | OCH(CH$_3$)$_2$ |
| A-707 | OCHFCl | I | OCH(CH$_3$)$_2$ |
| A-708 | OCF$_3$ | I | OCH(CH$_3$)$_2$ |
| A-709 | OC(=O)CH$_3$ | I | OCH(CH$_3$)$_2$ |
| A-710 | OC(=O)CH$_2$CH$_3$ | I | OCH(CH$_3$)$_2$ |
| A-711 | OH | OH | OCH(CH$_3$)$_2$ |
| A-712 | SH | OH | OCH(CH$_3$)$_2$ |
| A-713 | SCH$_3$ | OH | OCH(CH$_3$)$_2$ |
| A-714 | NH$_2$ | OH | OCH(CH$_3$)$_2$ |
| A-715 | OCH$_3$ | OH | OCH(CH$_3$)$_2$ |
| A-716 | OCHF$_2$ | OH | OCH(CH$_3$)$_2$ |
| A-717 | OCHFCl | OH | OCH(CH$_3$)$_2$ |
| A-718 | OCF$_3$ | OH | OCH(CH$_3$)$_2$ |
| A-719 | OC(=O)CH$_3$ | OH | OCH(CH$_3$)$_2$ |
| A-720 | OC(=O)CH$_2$CH$_3$ | OH | OCH(CH$_3$)$_2$ |
| A-721 | SH | SH | OCH(CH$_3$)$_2$ |
| A-722 | SCH$_3$ | SH | OCH(CH$_3$)$_2$ |
| A-723 | NH$_2$ | SH | OCH(CH$_3$)$_2$ |
| A-724 | OCH$_3$ | SH | OCH(CH$_3$)$_2$ |
| A-725 | OCHF$_2$ | SH | OCH(CH$_3$)$_2$ |
| A-726 | OCHFCl | SH | OCH(CH$_3$)$_2$ |
| A-727 | OCF$_3$ | SH | OCH(CH$_3$)$_2$ |
| A-728 | OC(=O)CH$_3$ | SH | OCH(CH$_3$)$_2$ |
| A-729 | OC(=O)CH$_2$CH$_3$ | SH | OCH(CH$_3$)$_2$ |
| A-730 | SCH$_3$ | SCH$_3$ | OCH(CH$_3$)$_2$ |
| A-731 | NH$_2$ | SCH$_3$ | OCH(CH$_3$)$_2$ |
| A-732 | OCH$_3$ | SCH$_3$ | OCH(CH$_3$)$_2$ |
| A-733 | OCHF$_2$ | SCH$_3$ | OCH(CH$_3$)$_2$ |
| A-734 | OCHFCl | SCH$_3$ | OCH(CH$_3$)$_2$ |
| A-735 | OCF$_3$ | SCH$_3$ | OCH(CH$_3$)$_2$ |
| A-736 | OC(=O)CH$_3$ | SCH$_3$ | OCH(CH$_3$)$_2$ |
| A-737 | OC(=O)CH$_2$CH$_3$ | SCH$_3$ | OCH(CH$_3$)$_2$ |
| A-738 | NH$_2$ | NH$_2$ | OCH(CH$_3$)$_2$ |
| A-739 | OCH$_3$ | NH$_2$ | OCH(CH$_3$)$_2$ |
| A-740 | OCHF$_2$ | NH$_2$ | OCH(CH$_3$)$_2$ |
| A-741 | OCHFCl | NH$_2$ | OCH(CH$_3$)$_2$ |
| A-742 | OCF$_3$ | NH$_2$ | OCH(CH$_3$)$_2$ |
| A-743 | OC(=O)CH$_3$ | NH$_2$ | OCH(CH$_3$)$_2$ |
| A-744 | OC(=O)CH$_2$CH$_3$ | NH$_2$ | OCH(CH$_3$)$_2$ |
| A-745 | OCH$_3$ | OCH$_3$ | OCH(CH$_3$)$_2$ |
| A-746 | OCHF$_2$ | OCH$_3$ | OCH(CH$_3$)$_2$ |
| A-747 | OCHFCl | OCH$_3$ | OCH(CH$_3$)$_2$ |
| A-748 | OCF$_3$ | OCH$_3$ | OCH(CH$_3$)$_2$ |
| A-749 | OC(=O)CH$_3$ | OCH$_3$ | OCH(CH$_3$)$_2$ |
| A-750 | OC(=O)CH$_2$CH$_3$ | OCH$_3$ | OCH(CH$_3$)$_2$ |
| A-751 | OCHF$_2$ | OCHF$_2$ | OCH(CH$_3$)$_2$ |
| A-752 | OCHFCl | OCHF$_2$ | OCH(CH$_3$)$_2$ |
| A-753 | OCF$_3$ | OCHF$_2$ | OCH(CH$_3$)$_2$ |
| A-754 | OC(=O)CH$_3$ | OCHF$_2$ | OCH(CH$_3$)$_2$ |
| A-755 | OC(=O)CH$_2$CH$_3$ | OCHF$_2$ | OCH(CH$_3$)$_2$ |
| A-756 | OCHFCl | OCHFCl | OCH(CH$_3$)$_2$ |
| A-757 | OCF$_3$ | OCHFCl | OCH(CH$_3$)$_2$ |
| A-758 | OC(=O)CH$_3$ | OCHFCl | OCH(CH$_3$)$_2$ |
| A-759 | OC(=O)CH$_2$CH$_3$ | OCHFCl | OCH(CH$_3$)$_2$ |
| A-760 | OCF$_3$ | OCF$_3$ | OCH(CH$_3$)$_2$ |
| A-761 | OC(=O)CH$_3$ | OCF$_3$ | OCH(CH$_3$)$_2$ |
| A-762 | OC(=O)CH$_2$CH$_3$ | OCF$_3$ | OCH(CH$_3$)$_2$ |
| A-763 | OC(=O)CH$_3$ | OC(=O)CH$_3$ | OCH(CH$_3$)$_2$ |
| A-764 | OC(=O)CH$_2$CH$_3$ | OC(=O)CH$_3$ | OCH(CH$_3$)$_2$ |
| A-765 | OC(=O)CH$_2$CH$_3$ | OC(=O)CH$_2$CH$_3$ | OCH(CH$_3$)$_2$ |
| A-766 | CH$_3$ | CH$_3$ | OCH$_2$CH$_2$CH$_2$CH$_3$ |
| A-767 | CH$_2$CH$_3$ | CH$_3$ | OCH$_2$CH$_2$CH$_2$CH$_3$ |
| A-768 | CF$_3$ | CH$_3$ | OCH$_2$CH$_2$CH$_2$CH$_3$ |
| A-769 | F | CH$_3$ | OCH$_2$CH$_2$CH$_2$CH$_3$ |
| A-770 | Cl | CH$_3$ | OCH$_2$CH$_2$CH$_2$CH$_3$ |
| A-771 | Br | CH$_3$ | OCH$_2$CH$_2$CH$_2$CH$_3$ |
| A-772 | I | CH$_3$ | OCH$_2$CH$_2$CH$_2$CH$_3$ |
| A-773 | OH | CH$_3$ | OCH$_2$CH$_2$CH$_2$CH$_3$ |
| A-774 | SH | CH$_3$ | OCH$_2$CH$_2$CH$_2$CH$_3$ |
| A-775 | SCH$_3$ | CH$_3$ | OCH$_2$CH$_2$CH$_2$CH$_3$ |
| A-776 | NH$_2$ | CH$_3$ | OCH$_2$CH$_2$CH$_2$CH$_3$ |
| A-777 | OCH$_3$ | CH$_3$ | OCH$_2$CH$_2$CH$_2$CH$_3$ |
| A-778 | OCHF$_2$ | CH$_3$ | OCH$_2$CH$_2$CH$_2$CH$_3$ |
| A-779 | OCHFCl | CH$_3$ | OCH$_2$CH$_2$CH$_2$CH$_3$ |
| A-780 | OCF$_3$ | CH$_3$ | OCH$_2$CH$_2$CH$_2$CH$_3$ |
| A-781 | OC(=O)CH$_3$ | CH$_3$ | OCH$_2$CH$_2$CH$_2$CH$_3$ |
| A-782 | OC(=O)CH$_2$CH$_3$ | CH$_3$ | OCH$_2$CH$_2$CH$_2$CH$_3$ |
| A-783 | CH$_2$CH$_3$ | CH$_2$CH$_3$ | OCH$_2$CH$_2$CH$_2$CH$_3$ |
| A-784 | CF$_3$ | CH$_2$CH$_3$ | OCH$_2$CH$_2$CH$_2$CH$_3$ |
| A-785 | F | CH$_2$CH$_3$ | OCH$_2$CH$_2$CH$_2$CH$_3$ |

TABLE A-continued

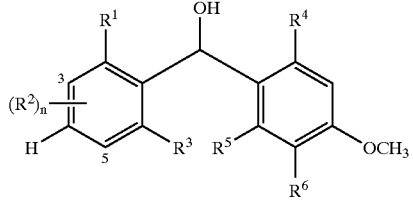

I-A

| No. | R¹ | R³ | R⁵ |
|---|---|---|---|
| A-786 | Cl | CH₂CH₃ | OCH₂CH₂CH₂CH₃ |
| A-787 | Br | CH₂CH₃ | OCH₂CH₂CH₂CH₃ |
| A-788 | I | CH₂CH₃ | OCH₂CH₂CH₂CH₃ |
| A-789 | OH | CH₂CH₃ | OCH₂CH₂CH₂CH₃ |
| A-790 | SH | CH₂CH₃ | OCH₂CH₂CH₂CH₃ |
| A-791 | SCH₃ | CH₂CH₃ | OCH₂CH₂CH₂CH₃ |
| A-792 | NH₂ | CH₂CH₃ | OCH₂CH₂CH₂CH₃ |
| A-793 | OCH₃ | CH₂CH₃ | OCH₂CH₂CH₂CH₃ |
| A-794 | OCHF₂ | CH₂CH₃ | OCH₂CH₂CH₂CH₃ |
| A-795 | OCHFCl | CH₂CH₃ | OCH₂CH₂CH₂CH₃ |
| A-796 | OCF₃ | CH₂CH₃ | OCH₂CH₂CH₂CH₃ |
| A-797 | OC(=O)CH₃ | CH₂CH₃ | OCH₂CH₂CH₂CH₃ |
| A-798 | OC(=O)CH₂CH₃ | CH₂CH₃ | OCH₂CH₂CH₂CH₃ |
| A-799 | CF₃ | CF₃ | OCH₂CH₂CH₂CH₃ |
| A-800 | F | CF₃ | OCH₂CH₂CH₂CH₃ |
| A-801 | Cl | CF₃ | OCH₂CH₂CH₂CH₃ |
| A-802 | Br | CF₃ | OCH₂CH₂CH₂CH₃ |
| A-803 | I | CF₃ | OCH₂CH₂CH₂CH₃ |
| A-804 | OH | CF₃ | OCH₂CH₂CH₂CH₃ |
| A-805 | SH | CF₃ | OCH₂CH₂CH₂CH₃ |
| A-806 | SCH₃ | CF₃ | OCH₂CH₂CH₂CH₃ |
| A-807 | NH₂ | CF₃ | OCH₂CH₂CH₂CH₃ |
| A-808 | OCH₃ | CF₃ | OCH₂CH₂CH₂CH₃ |
| A-809 | OCHF₂ | CF₃ | OCH₂CH₂CH₂CH₃ |
| A-810 | OCHFCl | CF₃ | OCH₂CH₂CH₂CH₃ |
| A-811 | OCF₃ | CF₃ | OCH₂CH₂CH₂CH₃ |
| A-812 | OC(=O)CH₃ | CF₃ | OCH₂CH₂CH₂CH₃ |
| A-813 | OC(=O)CH₂CH₃ | CF₃ | OCH₂CH₂CH₂CH₃ |
| A-814 | F | F | OCH₂CH₂CH₂CH₃ |
| A-815 | Cl | F | OCH₂CH₂CH₂CH₃ |
| A-816 | Br | F | OCH₂CH₂CH₂CH₃ |
| A-817 | I | F | OCH₂CH₂CH₂CH₃ |
| A-818 | OH | F | OCH₂CH₂CH₂CH₃ |
| A-819 | SH | F | OCH₂CH₂CH₂CH₃ |
| A-820 | SCH₃ | F | OCH₂CH₂CH₂CH₃ |
| A-821 | NH₂ | F | OCH₂CH₂CH₂CH₃ |
| A-822 | OCH₃ | F | OCH₂CH₂CH₂CH₃ |
| A-823 | OCHF₂ | F | OCH₂CH₂CH₂CH₃ |
| A-824 | OCHFCl | F | OCH₂CH₂CH₂CH₃ |
| A-825 | OCF₃ | F | OCH₂CH₂CH₂CH₃ |
| A-826 | OC(=O)CH₃ | F | OCH₂CH₂CH₂CH₃ |
| A-827 | OC(=O)CH₂CH₃ | F | OCH₂CH₂CH₂CH₃ |
| A-828 | Cl | Cl | OCH₂CH₂CH₂CH₃ |
| A-829 | Br | Cl | OCH₂CH₂CH₂CH₃ |
| A-830 | I | Cl | OCH₂CH₂CH₂CH₃ |
| A-831 | OH | Cl | OCH₂CH₂CH₂CH₃ |
| A-832 | SH | Cl | OCH₂CH₂CH₂CH₃ |
| A-833 | SCH₃ | Cl | OCH₂CH₂CH₂CH₃ |
| A-834 | NH₂ | Cl | OCH₂CH₂CH₂CH₃ |
| A-835 | OCH₃ | Cl | OCH₂CH₂CH₂CH₃ |
| A-836 | OCHF₂ | Cl | OCH₂CH₂CH₂CH₃ |
| A-837 | OCHFCl | Cl | OCH₂CH₂CH₂CH₃ |
| A-838 | OCF₃ | Cl | OCH₂CH₂CH₂CH₃ |
| A-839 | OC(=O)CH₃ | Cl | OCH₂CH₂CH₂CH₃ |
| A-840 | OC(=O)CH₂CH₃ | Cl | OCH₂CH₂CH₂CH₃ |
| A-841 | Br | Br | OCH₂CH₂CH₂CH₃ |
| A-842 | I | Br | OCH₂CH₂CH₂CH₃ |
| A-843 | OH | Br | OCH₂CH₂CH₂CH₃ |
| A-844 | SH | Br | OCH₂CH₂CH₂CH₃ |
| A-845 | SCH₃ | Br | OCH₂CH₂CH₂CH₃ |
| A-846 | NH₂ | Br | OCH₂CH₂CH₂CH₃ |
| A-847 | OCH₃ | Br | OCH₂CH₂CH₂CH₃ |
| A-848 | OCHF₂ | Br | OCH₂CH₂CH₂CH₃ |
| A-849 | OCHFCl | Br | OCH₂CH₂CH₂CH₃ |
| A-850 | OCF₃ | Br | OCH₂CH₂CH₂CH₃ |
| A-851 | OC(=O)CH₃ | Br | OCH₂CH₂CH₂CH₃ |
| A-852 | OC(=O)CH₂CH₃ | Br | OCH₂CH₂CH₂CH₃ |
| A-853 | I | I | OCH₂CH₂CH₂CH₃ |
| A-854 | OH | I | OCH₂CH₂CH₂CH₃ |
| A-855 | SH | I | OCH₂CH₂CH₂CH₃ |
| A-856 | SCH₃ | I | OCH₂CH₂CH₂CH₃ |
| A-857 | NH₂ | I | OCH₂CH₂CH₂CH₃ |
| A-858 | OCH₃ | I | OCH₂CH₂CH₂CH₃ |
| A-859 | OCHF₂ | I | OCH₂CH₂CH₂CH₃ |
| A-860 | OCHFCl | I | OCH₂CH₂CH₂CH₃ |
| A-861 | OCF₃ | I | OCH₂CH₂CH₂CH₃ |
| A-862 | OC(=O)CH₃ | I | OCH₂CH₂CH₂CH₃ |
| A-863 | OC(=O)CH₂CH₃ | I | OCH₂CH₂CH₂CH₃ |
| A-864 | OH | OH | OCH₂CH₂CH₂CH₃ |
| A-865 | SH | OH | OCH₂CH₂CH₂CH₃ |
| A-866 | SCH₃ | OH | OCH₂CH₂CH₂CH₃ |
| A-867 | NH₂ | OH | OCH₂CH₂CH₂CH₃ |
| A-868 | OCH₃ | OH | OCH₂CH₂CH₂CH₃ |
| A-869 | OCHF₂ | OH | OCH₂CH₂CH₂CH₃ |
| A-870 | OCHFCl | OH | OCH₂CH₂CH₂CH₃ |
| A-871 | OCF₃ | OH | OCH₂CH₂CH₂CH₃ |
| A-872 | OC(=O)CH₃ | OH | OCH₂CH₂CH₂CH₃ |
| A-873 | OC(=O)CH₂CH₃ | OH | OCH₂CH₂CH₂CH₃ |
| A-874 | SH | SH | OCH₂CH₂CH₂CH₃ |
| A-875 | SCH₃ | SH | OCH₂CH₂CH₂CH₃ |
| A-876 | NH₂ | SH | OCH₂CH₂CH₂CH₃ |
| A-877 | OCH₃ | SH | OCH₂CH₂CH₂CH₃ |
| A-878 | OCHF₂ | SH | OCH₂CH₂CH₂CH₃ |
| A-879 | OCHFCl | SH | OCH₂CH₂CH₂CH₃ |
| A-880 | OCF₃ | SH | OCH₂CH₂CH₂CH₃ |
| A-881 | OC(=O)CH₃ | SH | OCH₂CH₂CH₂CH₃ |
| A-882 | OC(=O)CH₂CH₃ | SH | OCH₂CH₂CH₂CH₃ |
| A-883 | SCH₃ | SCH₃ | OCH₂CH₂CH₂CH₃ |
| A-884 | NH₂ | SCH₃ | OCH₂CH₂CH₂CH₃ |
| A-885 | OCH₃ | SCH₃ | OCH₂CH₂CH₂CH₃ |
| A-886 | OCHF₂ | SCH₃ | OCH₂CH₂CH₂CH₃ |
| A-887 | OCHFCl | SCH₃ | OCH₂CH₂CH₂CH₃ |
| A-888 | OCF₃ | SCH₃ | OCH₂CH₂CH₂CH₃ |
| A-889 | OC(=O)CH₃ | SCH₃ | OCH₂CH₂CH₂CH₃ |
| A-890 | OC(=O)CH₂CH₃ | SCH₃ | OCH₂CH₂CH₂CH₃ |
| A-891 | NH₂ | NH₂ | OCH₂CH₂CH₂CH₃ |
| A-892 | OCH₃ | NH₂ | OCH₂CH₂CH₂CH₃ |
| A-893 | OCHF₂ | NH₂ | OCH₂CH₂CH₂CH₃ |
| A-894 | OCHFCl | NH₂ | OCH₂CH₂CH₂CH₃ |
| A-895 | OCF₃ | NH₂ | OCH₂CH₂CH₂CH₃ |
| A-896 | OC(=O)CH₃ | NH₂ | OCH₂CH₂CH₂CH₃ |
| A-897 | OC(=O)CH₂CH₃ | NH₂ | OCH₂CH₂CH₂CH₃ |
| A-898 | OCH₃ | OCH₃ | OCH₂CH₂CH₂CH₃ |
| A-899 | OCHF₂ | OCH₃ | OCH₂CH₂CH₂CH₃ |
| A-900 | OCHFCl | OCH₃ | OCH₂CH₂CH₂CH₃ |
| A-901 | OCF₃ | OCH₃ | OCH₂CH₂CH₂CH₃ |
| A-902 | OC(=O)CH₃ | OCH₃ | OCH₂CH₂CH₂CH₃ |
| A-903 | OC(=O)CH₂CH₃ | OCH₃ | OCH₂CH₂CH₂CH₃ |
| A-904 | OCHF₂ | OCHF₂ | OCH₂CH₂CH₂CH₃ |
| A-905 | OCHFCl | OCHF₂ | OCH₂CH₂CH₂CH₃ |
| A-906 | OCF₃ | OCHF₂ | OCH₂CH₂CH₂CH₃ |
| A-907 | OC(=O)CH₃ | OCHF₂ | OCH₂CH₂CH₂CH₃ |
| A-908 | OC(=O)CH₂CH₃ | OCHF₂ | OCH₂CH₂CH₂CH₃ |
| A-909 | OCHFCl | OCHFCl | OCH₂CH₂CH₂CH₃ |
| A-910 | OCF₃ | OCHFCl | OCH₂CH₂CH₂CH₃ |
| A-911 | OC(=O)CH₃ | OCHFCl | OCH₂CH₂CH₂CH₃ |
| A-912 | OC(=O)CH₂CH₃ | OCHFCl | OCH₂CH₂CH₂CH₃ |
| A-913 | OCF₃ | OCF₃ | OCH₂CH₂CH₂CH₃ |
| A-914 | OC(=O)CH₃ | OCF₃ | OCH₂CH₂CH₂CH₃ |

TABLE A-continued

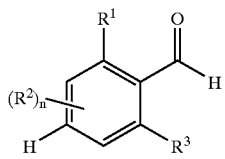

| No. | R$^1$ | R$^3$ | R$^5$ |
|---|---|---|---|
| A-915 | OC(=O)CH$_2$CH$_3$ | OCF$_3$ | OCH$_2$CH$_2$CH$_2$CH$_3$ |
| A-916 | OC(=O)CH$_3$ | OC(=O)CH$_3$ | OCH$_2$CH$_2$CH$_2$CH$_3$ |
| A-917 | OC(=O)CH$_2$CH$_3$ | OC(=O)CH$_3$ | OCH$_2$CH$_2$CH$_2$CH$_3$ |
| A-918 | OC(=O)CH$_2$CH$_3$ | OC(=O)CH$_2$CH$_3$ | OCH$_2$CH$_2$CH$_2$CH$_3$ |

The compounds of the formula I can be obtained by different routes. Compounds of the formula I in which X is oxygen are obtained, for example, by reacting aldehydes of the formula II,

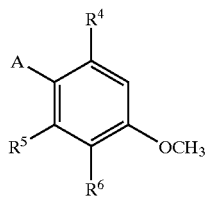

where the variables R$^1$, R$^2$, R$^3$ and n are as defined for formula I and may be protected by a protective group Q which is removed after the reaction, with halobenzene derivatives of the formula III,

III where the variables R$^4$, R$^5$ and R$^6$ are as defined for formula I and A is halogen, and A is converted, in an intermediate step, into a group B, where B is a suitable metal or a suitable halometal group.

Suitable groups A are fluorine, chlorine, bromine or iodine, preferably chlorine or bromine.

Suitable groups B are, for example, Li, Na, MgY (Y=halogen, in particular Br), Sn(R')$_2$ (R'=CH$_3$, CH$_2$CH$_3$), ZnR', Cu(CN)ZnI [cf. J. March, Advanced Organic Chemistry, J. Wiley & Sons, New York, 1992, pp. 920–929 and the literature cited therein].

Preferred groups B are Na and MgY.

The reaction is carried out by converting the halogen group A into the group B in a manner known per se, followed by in situ reaction of the resulting benzene derivatives with aldehydes of the formula II [cf. J. March, Advanced Organic Chemistry, J. Wiley & Sons, New York, 1992, pp. 920–929 and the literature cited therein].

If B is Li, Na or MgY, the reaction is carried out, for example, at temperatures of from −20° C. to 150° C., preferably from 20° C. to 100° C., in an inert organic solvent, using at least equimolar amounts of Li, Na or Mg, based on the halobenzene III, and, if B is Li or Na, if appropriate under reaction-accelerating conditions, such as the addition of dibromoethane or iodine, or the use of ultrasound [cf. J. March, Advanced Organic Chemistry, J. Wiley & Sons, New York, 1992, pp. 920–929 and the literature cited therein].

The protective group Q is introduced into the aldehydes of the formula II by methods known from the literature [cf. T. W. Greene, Protective Groups in Organic Chemistry, J. Wiley & Sons, 1991, pp. 10–142].

Suitable protective groups for R$^1$, R$^2$, R$^3$=hydroxyl, mercapto or amino are, for example, groups that can be removed under Lewis-acidic conditions, such as alkyl, in particular methyl.

In a preferred embodiment of the reaction, the variables R$^1$, R$^2$ and R$^3$ are inert under the reaction conditions.

For preparing compounds I in which R$^1$ and R$^3$ contain carbonyl functionalities, the process described below, which uses the corresponding benzophenones IV as starting materials, is preferred.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitrites, such as acetonitrile and propionitrile, preferably ethers, very particularly preferably diethyl ether and tetrahydrofuran.

It is also possible to use mixtures of the solvents mentioned.

The starting materials are generally reacted with one another in equimolar amounts. In terms of yield, it may be advantageous to use an excess of compounds of the formula III, based on compounds of the formula II.

The reaction mixtures are worked up in a customary manner, for example by mixing with water, phase separation and, if required, chromatographic purification of the crude products. Some intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

The starting materials of the formula II required for preparing the compounds I can be prepared, for example, by reducing the corresponding benzoic acids or benzoic esters with diisobutylaluminum hydride, described, for example, in EP-A 727 141, or they can be prepared in the manner known per se [cf. J. March, Advanced Organic Chemistry, J. Wiley & Sons, New York, 1992, pp. 501–521, pp 641–758, pp. 982–1161.].

The starting materials of the formula III required for preparing the compounds I can be prepared by methods known from the literature from gallic acid or its derivatives, or in a manner known per se [cf. J. March, Advanced Organic Chemistry, J. Wiley & Sons, New York, 1992, pp. 501–521, pp. 641–758, pp. 982–1161.].

Compounds of the formula I in which X is oxygen can also be prepared by reduction of the analogous benzophenone derivatives of the formula IV,

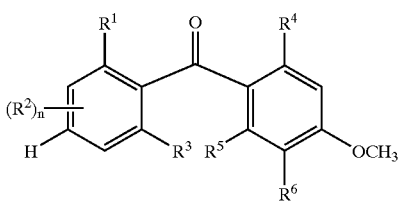

where the variables are as defined for formula I or denote a group which, after the reaction, can be converted into these radicals, using hydrides or by catalytic reduction with $H_2$.

Suitable hydrides are, preferably, borohydrides and aluminum hydrides, such as $NaBH_4$ or $LiAlH_4$ [cf. M. Hudlicky, Reductions in Organic Chemistry, ACS Monograph 188, American Chemical Society, Washington D.C., 1996, p. 152 ff.; Tetrahedron Lett. 28 (4), pp. 4725–4728 (1987)], or elemental aluminum in ammonia [cf. Chem. Soc. Jpn. 63(1), pp. 290–292 (1990)].

The reaction is usually carried out at temperatures of from −78° C. to 120° C., preferably from −78° C. to 0° C., in an inert organic solvent.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, preferably ethers, articularly preferably tetrahydrofuran. It is also possible to use mixtures of the solvents mentioned.

The starting materials are generally reacted with one another in equimolar amounts. In terms of yield, it may be advantageous to employ an excess of reducing agent, based on compounds of the formula IV.

The reaction mixtures are worked up in a customary manner, for example by mixing with water, phase separation and, if required, chromatographic purification of the crude products. Some intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

The reduction can also be carried out in the manner known per se using $H_2$ and catalysts based on transition metals. Suitable transition metals are palladium, platinum, rhodium and ruthenium.

This reaction is usually carried out at temperatures of from 0° C. to 150° C., preferably from 0° C. to 50° C., in an inert organic solvent [cf. Organotransition Metal Chemistry, Academic Press, New York, 1974, pp. 65–70 and the literature cited therein; JP-A 10273455].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, alcohols, such as methanol, ethanol, n-propanol, isopropanol, n-butanol and tert-butanol, particularly preferably methanol, ethanol or isopropanol. It is also possible to use mixtures of the solvents mentioned.

In a preferred embodiment of the reduction with $H_2$, chiral catalysts are employed, so that it is possible to obtain the (R) or (S) isomer of the benzhydryl alcohol I in a selective manner [cf. Org. Lett. 2(5), pp. 659–662, (2000)].

If the variables $R^1$, $R^2$ or $R^3$ are groups which can be reduced under the reaction conditions, such as nitro or formyl, it may be necessary to re-establish these groups after the reaction by selective oxidation. It may also be advantageous to introduce such reducible groups only after the reduction of the benzophenones IV has taken place, by oxidizing appropriate groups (for example introducing a nitro group by oxidation of an amino group or introducing a formyl group by oxidation of a hydroxyl group).

Compounds I in which $R^1$ is formyl can be obtained, for example, by selective oxidation of corresponding compounds in which $R^1$ is hydroxymethyl, which may be formed in the reduction according to the invention from a formyl group [cf. M. Hudlicky, Oxidations in Organic Chemistry, ACS Monograph 186, American Chemical Society, Washington D.C., 1990, pp. 114–127].

It may also be advantageous to obtain compounds of the formula I in which $R^1$ is hydroxyl by reducing compounds of the formula IV in which $R^1$ is alkylcarbonyloxy. Here, $R^1$ and the keto group that bridges the phenyl groups are reduced simultaneously.

For compounds I in which the variables $R^1$, $R^2$, $R^3$ or $R^4$ are alkenyl or alkynyl, the process described above, which uses halobenzene derivatives III and aldehydes II as starting materials, is preferred.

The reaction mixtures are worked up in a customary manner, for example by mixing with water, phase separation and, if required, chromatographic purification of the crude products. Some intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

The starting materials of the formula IV required for preparing the compounds I are known from the literature (for example from EP-A 727 141), or they can be prepared in accordance with the literature cited.

If individual compounds I are not accessible by the routes described above, they can be prepared by derivatization of other compounds I.

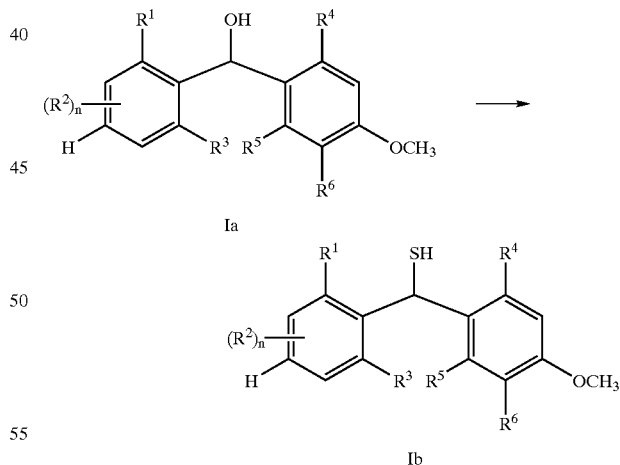

The benzhydryl thiols Ib can be obtained from the corresponding alcohols Ia under conditions known from the literature. The reaction is usually carried out at temperatures of from 0° C. to 180° C., preferably from 20° C. to 140° C., in an inert organic solvent [cf. Liebigs Ann. Chem., p. 177 (1989)].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, and dimethylene glycol, particularly preferably toluene and dimethylene glycol.

It is also possible to use mixtures of the solvents mentioned.

Suitable sulfurizing agents are, for example, phosphorus pentasulfide or Lawesson's reagent.

The starting materials are generally reacted with one another in equimolar amounts. In terms of yield, it may be advantageous to employ an excess of sulfurizing agent, based on Ia.

Benzhydryl thiols Ib can also be obtained by reducing the corresponding thioketones V, which can be prepared from the benzophenones IV.

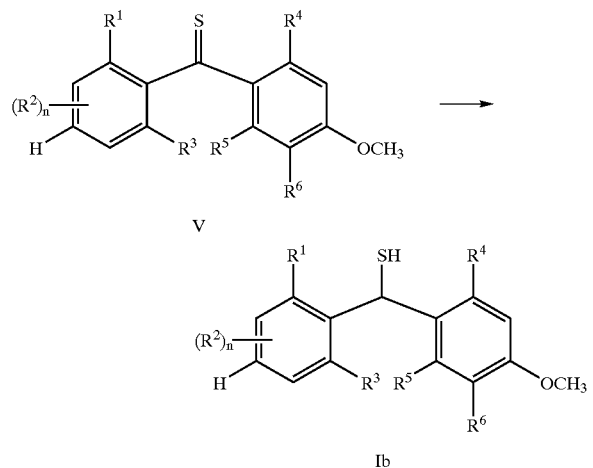

The reduction to give the benzhydryl thiols Ib can be carried out using, for example, borohydrides or aluminum hydrides [cf. Synth. Commun. 23 (9), pp. 1267–1271 (1993); Tetrahedron: Asymmetry 7(12), pp. 3553–3558 (1996); Can. J. Chem. 48, p. 3593, (1970)], or using elemental ytterbium in tetrahydrofuran [cf. Chem. Lett. 3, p. 611 (1994)].

The conversion of the benzophenones IV into the thioketones V is carried out analogously to the reaction of the benzhydryl alcohols Ia described above.

The compounds I are suitable as fungicides. They have excellent activity against a broad spectrum of phytopathogenic fungi, in particular from the class of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soya, coffee, sugar cane, grape vines, fruit species, ornamentals and vegetable species such as cucumbers, beans, tomatoes, potatoes and cucurbits, and also in the seeds of these plants.

Specifically, they are suitable for controlling the following plant diseases:

Alternaria species in vegetables and fruit,
Botrytis cinerea (gray mold) in strawberries, vegetables, ornamentals and grape vines,
Cercospora arachidicola in groundnuts,
Erysiphe cichoracearum and Sphaerotheca fuliginea in cucurbits,
Erysiphe graminis (powdery mildew) in cereals,
Fusarium and Verticillium species in a variety of plants,
Helminthosporium species in cereals,
Mycosphaerella species in bananas and groundnuts,
Phytophthora infestans in potatoes and tomatoes,
Plasmopara viticola in grape vines,
Podosphaera leucotricha in apples,
Pseudocercosporella herpotrichoides in wheat and barley,
Pseudoperonospora species in hops and cucumbers,
Puccinia species in cereals,
Pyricularia oryzae in rice,
Rhizoctonia species in cotton, rice and lawns,
Septoria nodorum in wheat,
Uncinula necator in grape vines,
Ustilago species in cereals and sugar cane, and
Venturia species (scab) in apples and pears.

The compounds I are also suitable for controlling harmful fungi such as Paecilomyces variotii in the protection of materials (for example wood, paper, paint dispersions, fibers or tissues) and in the protection of stored products.

The compounds I are employed by treating the fungi or the plants, seeds, materials to be protected against fungal attack or the soil with a fungicidally effective amount of the active compounds. The application may be carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it also being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel oil, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone and water.

Powders, compositions for broadcasting and dusts can be prepared by mixing or jointly grinding the active substances with a solid carrier.

Granules, for example coated granules, impregnated granules and homogeneous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of Formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100 000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20 000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusting compositions, compositions for broadcasting, or granules, by spraying, atomizing, dusting, broadcasting or watering. The application forms depend entirely on the intended uses; in any case, they should ensure the finest dispersion possible of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

a sulfur, dithiocarbamates and their derivatives, such as iron(III) dimethyldithiocarbamate, zinc dimethyldithio-carbamate, zinc ethylenebisdithiocarbamate, manganese ethylenebisdithiocarbamate, manganese zinc ethylenediamine-bisdithiocarbamate, tetramethylthiuram disulfides, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis-(thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo-[4,5-b]quinoxaline, methyl 1-(butylcarbamoyl)-2-benzimidazole-carbamate, 2-methoxycarbonylaminobenzimidazole, 2-(furyl-(2))-benzimidazole, 2-(thiazolyl-(4))-benzimidazole, N-(1,1,2,2-tetrachloroethylthio)tetrahydrophthalimide, N-trichloromethylthiotetrahydrophthalimide, N-trichloro-methylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethyl-furan-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)-formamide, 1-(3,4-dichloroanilino)-1-formylamino-2,2,2-tri-chloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl) -α-(4-chlorophenyl) -5-pyrimidinemethanol, 5-butyl-2-dimethylamino-4-hydroxy-6-methylpyrimidine, bis-(p-chlorophenyl)-3-pyridinemethanol, 1,2-bis(3-ethoxycarbonyl-2-thioureido)benzene, 1,2-bis-(3-methoxycarbonyl-2-thioureido)-benzene, strobilurins, such as methyl E-methoxyimino[α-(o-tolyloxy)-o-tolyl]acetate, methyl E-2-{2-[6-(2-cyanophenoxy)-pyrimidin-4-yloxy]phenyl}-3-methoxyacrylate, methyl E-methoxyimino-[α-(2-phenoxyphenyl)]acetamide, methyl E-methoxyimino-[α-(2,5-dimethylphenoxy)-o-tolyl]acetamide, methyl E-2-{2-[(2-trifluoromethylpyrid-6-yl)oxymethyl]phenyl}-3-methoxyacrylate, methyl (E,E)-methoximino-{2-[1-(3-trifluoro-methylphenyl)ethylideneaminooxymethyl]phenyl}acetate, methyl N-(2-{[1-(4-chlorophenyl)-1H-pyrazol-3-yl]oxymethyl}phenyl)-N-methoxycarbamate, anilinopyrimidines, such as N-(4,6-dimethylpyrimidin-2-yl)aniline, N-[4-methyl-6-(l-propynyl)pyrimidin-2-yl]aniline, N-[4-methyl-6-cyclopropylpyrimidin-2-yl]aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxy-phenyl)acryloylmorpholine, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenyl-acetyl)alanine methyl ester, 5-methyl-5-vinyl-3-(3,5-dichloro-phenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl carbamoylhydantoin, N-(3,5-dichlorophenyl)-1,2-dimethylcyclopropane-1,2-dicarboximide, 2-cyano-[N-(ethylaminocarbonyl)-2-meth-oximino]acetamide, 1-[2-(2,4-dichlorophenyl)pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethyl-phenyl)-5-trifluoromethyl-3-chloro-2-aminopyridine, 1-((bis-(4-fluorophenyl)methylsilyl)methyl)-1H-1,2,4-triazole.

SYNTHESIS EXAMPLES

The procedures given in the synthesis examples below were used to obtain further compounds I by appropriate modification of the starting materials. The compounds obtained in this manner are listed in the tables which follow, together with physical data.

Example 1

Preparation of 5-bromo-6,6'-dimethyl-2,2', 3', 4'-tetramethoxybenz-hydryl alcohol

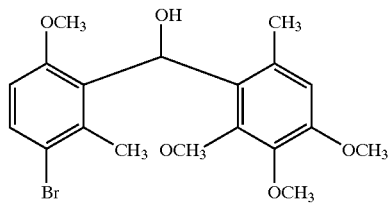

I-1

2.36 g of 2,3,4-trimethoxy-6-methylbromobenzene and 0.32 g of agnesium turnings were initially charged in 5 ml of anhydrous tetrahydrofuran, 0.57 ml of 1,2-dibromoethane was added and the reaction mixture was heated at reflux temperature for about 40 min. After cooling to 30° C., 1.40 g of 5-bromo-2-methoxy-6-methylbenzaldehyde were added dropwise, and the solution was stirred for about two hours. Water/2N hydrochloric acid (1/1) was added, the aqueous phase was extracted with ethyl acetate, the organic phases were washed with water and dried and the solvent was distilled off, and the residue was then purified by column chromatography (mobile phase petroleum ether/ethyl acetate 85/5). 1.5 g of the title compound were isolated as a violet viscous oil.

Example 2

Preparation of 2,5-dichloro-6,6'-dimethyl-2', 3', 4'-trimethoxy-benzhydryl alcohol

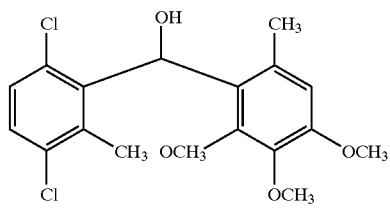

I-2

Under protective gas conditions, at about −78° C., 1 ml of a 1-molar solution of LiAlH$_4$ in tetrahydrofuran was added dropwise to a solution of 0.37 g of 2,5-dichloro-6,6'-dimethyl-2', 3', 4'-trimethoxybenzophenone in 20 ml of anhydrous tetrahydrofuran, and the mixture was stirred for about 1 hour. At 20–25° C., sat. NaHCO$_3$ solution was added to the reaction solution, the solution was extracted with ethyl acetate and the organic phase was washed with water and sat. NaCl solution and dried, and the solvent was then distilled off. The residue gave, after purification by column chromatography (mobile phase: ethyl acetate/cyclohexane 1:9), 150 mg of the title compound as a yellow viscous oil.

Example 3

Preparation of 5-chloro-2-hydroxy-6,6'-dimethyl-2', 3', 4'-trimethoxybenzhydryl alcohol

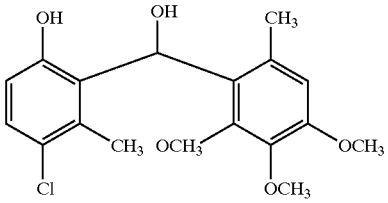

I-3

At −20° C., under an atmosphere of protective gas, 3 mmol of a 1-molar solution of LiAlH$_4$ in tetrahydrofuran (THF) were added dropwise to a solution of 0.86 g of 5-chloro-2-hydroxy-6,6'-dimethyl-2', 3', 4'-trimethoxybenzophenone in 10 ml of anhydrous THF. The reaction mixture was warmed to room temperature and then admixed with ice water, acidified with dilute hydrochloric acid and extracted with ethyl acetate. The combined organic phases were washed with sat. NaCl solution, dried and purified by column chromatography (mobile phase: ethyl acetate/cyclohexane 3:7). This gave 0.46 mg of the title compound as a white solid of m.p. 140–142° C.

TABLE I

| No. | $R^1$ | $(R^2)_n$ | $R^3$ | $R^4$ | $R^5$ | $R^6$ | phys. data (m.p.[° C.]) |
|---|---|---|---|---|---|---|---|
| I-1 | OCH$_3$ | 5-Br | CH$_3$ | CH$_3$ | OCH$_3$ | OCH$_3$ | oil |
| I-2 | Cl | 5-Cl | CH$_3$ | CH$_3$ | OCH$_3$ | OCH$_3$ | oil |
| I-3 | OH | 5-Cl | CH$_3$ | CH$_3$ | OCH$_3$ | OCH$_3$ | 140–142 |

Examples of the Activity Against Harmful Fungi

The fungicidal activity of the compounds of the formula I was demonstrated by the following experiments:

The active compounds were formulated, separately or together, as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil) and diluted with water to the desired concentration.

After conclusion of the tests, in each case the lowest concentration at which the compounds still caused 80–100% inhibition in comparison to untreated controls (activity threshold or minimum concentration) was determined.

Use Example 1

Activity Against Mildew of Wheat

Leaves of potted wheat seedlings cv. "Kanzler" were sprayed to runoff point with an aqueous preparation of active compound which had been prepared from a stock solution made of 10% of active compound, 63% of cyclohexanone and 27% of emulsifier. 24 hours after the spray coating had dried on, the leaves were dusted with spores of mildew of wheat (Erysiphe graminis forma specialis tritici). The test plants were then placed in a greenhouse at 20–24° C. and 60–90% rel. atmospheric humidity. After 7 days, the extent of the mildew development was determined visually as % infection of the total leaf area.

In this test, the plants which had been treated with 4 or 16 ppm of the active compounds I-1, I-2 and 1–3 showed an infection of in each case at most 30%, whereas the untreated plants were infected to 90%.

We claim:

1. A fungicidally active benzhydryl derivative of the formula I,

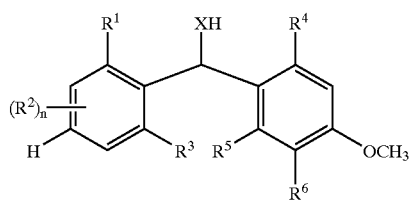

where the index and the variables are as defined below:
- X is oxygen or sulfur;
- $R^1, R^3$ are halogen, cyano, nitro, hydroxyl, mercapto, amino, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkylcarbonyloxy, formyloxy, $C_1$–$C_6$-alkylthio, $C_2$–$C_6$-alkenylthio, $C_2$–$C_6$-alkynylthio, $C_1$–$C_6$-alkylamino, $C_1$–$C_6$-alkylcarbonyl or formyl, where the carbon atoms in the radicals mentioned may be partially or fully halogenated;
- $R^2$ is halogen, cyano, nitro, hydroxyl, mercapto, amino, $C_1$–$C_6$-alkyl, $C_1$–$C_6$-alkoxy, $C_1$–$C_6$-haloalkyl or $C_1$–$C_6$-haloalkoxy, where the groups $R^2$ may be different if n=2;
- $R^4$ is $C_1$–$C_6$-alkyl or $C_1$–$C_6$-haloalkyl;
- $R^5, R^6$ are hydroxyl, $C_1$–$C_6$-alkyl, $C_1$–$C_6$-alkoxy, $C_2$–$C_6$-alkenyloxy, $C_1$–$C_6$-haloalkoxy, or $C_2$–$C_6$-haloalkenyloxy,
- n is 0, 1, or 2.

2. A compound of the formula I as claimed in claim 1 where X is oxygen.

3. A compound of the formula I as claimed in claim 1 where the variables are as defined below:
- $R^1, R^3$ independently of one another are halogen, hydroxyl, amino, mercapto, nitro, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylcarbonyloxy, $C_1$–$C_6$-haloalkylcarbonyloxy, $C_1$–$C_6$-alkylthio, $C_1$–$C_6$-haloalkylthio, $C_1$–$C_6$-alkylcarbonyl or $C_1$–$C_6$-haloalkylcarbonyl.

4. A compound of the formula I as claimed in claim 1 where
- $R^2$ is halogen, hydroxyl, $C_1$–$C_6$-alkyl, $C_1$–$C_6$-haloalkyl, $C_1$–$C_6$-alkoxy or $C_1$–$C_6$-haloalkoxy.

5. A compound of the formula I as claimed in claim 1, where the variables are as defined below:
- $R^1, R^3$ are halogen, hydroxyl, amino, mercapto, $C_1$–$C_6$-alkyl, $C_1$–$C_6$-haloalkyl, $C_1$–$C_6$-alkoxy, $C_1$–$C_6$-haloalkoxy or $C_1$–$C_6$-alkylcarbonyl;
- $R^2$ is halogen, hydroxyl, $C_1$–$C_6$-alkyl, $C_1$–$C_6$-haloalkyl, $C_1$–$C_6$-alkoxy or $C_1$–$C_6$-haloalkoxy;

$R^4$ is methyl;
$R^5, R^6$ are $C_1$–$C_6$-alkoxy;
n is 0 or 1.

6. A process for preparing compounds of the formula I as claimed in claim 1 in which X is oxygen, by reacting aldehydes of the formula II,

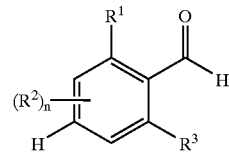

where the variables $R^1$, $R^2$, $R^3$ and n are as defined for formula I and may be protected by a protective group Q which is removed after the reaction, with halobenzene derivatives of the formula III,

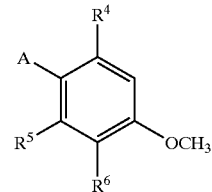

where the variables $R^4$, $R^5$ and $R^6$ are as defined for formula I and A is halogen, and A is converted, in an intermediate step, into a group B, where B is a suitable metal or a suitable halometal group.

7. A process for preparing compounds of the formula I as claimed in claim 1 in which X is oxygen, by reduction of benzophenone derivatives of the formula IV,

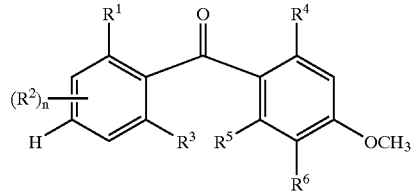

where the variables are as defined for formula I or denote a group which, after the reaction, can be converted into these radicals using hydrides or by catalytic reduction with $H_2$.

8. A composition suitable for controlling phytopathogenic harmful fungi, which comprises a solid or liquid carrier and a compound of the formula I as claimed in claim 1.

9. A method for controlling phytopathogenic fungi, which comprises treating the fungi or the materials, plants, the soil or the seed to be protected against fungal attack with an effective amount of a compound of the formula I as claimed in claim 1.

* * * * *